US011710261B2

United States Patent
Kim et al.

(10) Patent No.: US 11,710,261 B2
(45) Date of Patent: Jul. 25, 2023

(54) SCAN-SPECIFIC RECURRENT NEURAL NETWORK FOR IMAGE RECONSTRUCTION

(71) Applicant: University of Southern California, Los Angeles, CA (US)

(72) Inventors: Tae Hyung Kim, Los Angeles, CA (US); Justin Haldar, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 332 days.

(21) Appl. No.: 16/939,535

(22) Filed: Jul. 27, 2020

(65) Prior Publication Data

US 2021/0035337 A1    Feb. 4, 2021

Related U.S. Application Data

(60) Provisional application No. 62/879,982, filed on Jul. 29, 2019.

(51) Int. Cl.
| | |
|---|---|
| *G06T 11/00* | (2006.01) |
| *G16H 30/20* | (2018.01) |
| *G06N 3/08* | (2023.01) |
| *G06N 3/044* | (2023.01) |

(52) U.S. Cl.
CPC ............ *G06T 11/005* (2013.01); *G06N 3/044* (2023.01); *G06N 3/08* (2013.01); *G16H 30/20* (2018.01); *G06T 2210/41* (2013.01)

(58) Field of Classification Search
None
See application file for complete search history.

(56) References Cited

U.S. PATENT DOCUMENTS

| 6,421,612 B1 * | 7/2002 | Agrafiotis | G06K 9/6251 |
| | | | 702/19 |
| 10,712,416 B1 * | 7/2020 | Sandino | G16H 30/40 |
| 2007/0094168 A1 * | 4/2007 | Ayala | G06N 3/105 |
| | | | 706/15 |

(Continued)

OTHER PUBLICATIONS

Lee D, Yoo J, Tak S, Ye JC. Deep residual learning for accelerated MRI using magnitude and phase networks. IEEE Transactions on Biomedical Engineering. Apr. 2, 2018;65(9):1985-95. (Year: 2018).*

(Continued)

*Primary Examiner* — Michelle M Entezari

(74) *Attorney, Agent, or Firm* — Snell & Wilmer L.L.P.

(57) ABSTRACT

Methods, systems, devices and apparatuses for generating a high-quality MRI image from under-sampled or corrupted data The image reconstruction system includes a memory. The memory is configured to store multiple samples of biological, physiological, neurological or anatomical data that has missing or corrupted k-space data and a deep learning model or neural network. The image reconstruction system includes a processor coupled to the memory. The processor is configured to obtain the multiple samples. The processor is configured to determine the missing or corrupted k-space data using the multiple samples and the deep learning model or neural network. The processor is configured to reconstruct an MRI image using the determined missing or corrupted k-space data and the multiple samples.

16 Claims, 17 Drawing Sheets

(56) References Cited

U.S. PATENT DOCUMENTS

| | | | |
|---|---|---|---|
| 2011/0089946 A1* | 4/2011 | Griswold | G01R 33/4824 |
| | | | 324/309 |
| 2012/0133361 A1* | 5/2012 | Gross | G01R 33/5611 |
| | | | 324/309 |
| 2017/0236053 A1* | 8/2017 | Lavigueur | G06N 3/045 |
| | | | 706/31 |
| 2018/0293762 A1* | 10/2018 | Fu | G06T 11/003 |
| 2019/0041481 A1* | 2/2019 | Subbarao | G01R 33/3415 |
| 2019/0066268 A1* | 2/2019 | Song | G06N 3/0454 |
| 2019/0080456 A1* | 3/2019 | Song | G06T 7/174 |
| 2019/0313895 A1* | 10/2019 | Hayashi | G06N 3/0454 |
| 2019/0378271 A1* | 12/2019 | Takeshima | G16H 30/00 |
| 2019/0378311 A1* | 12/2019 | Mailhe | G16H 30/40 |
| 2020/0151510 A1* | 5/2020 | Vishnu | G06K 9/6231 |
| 2020/0184647 A1* | 6/2020 | Harrison | G16H 30/40 |
| 2020/0202586 A1* | 6/2020 | Li | G06T 11/003 |
| 2020/0387704 A1* | 12/2020 | Ng | G06V 10/82 |
| 2020/0397334 A1* | 12/2020 | Fang | A61B 5/7267 |
| 2020/0405269 A1* | 12/2020 | Swisher | A61B 8/4444 |

OTHER PUBLICATIONS

Akçkaya M, Moeller S, Weingärtner S, Uğurbil K. Scan-specific robust artificial-neural-networks for k-space interpolation (RAKI) reconstruction: Database-free deep learning for fast imaging. Magnetic resonance in medicine. Jan. 2019;81(1):439-53. (Year: 2019).*

Lustig, Michael, and John M. Pauly. "SPIRiT: iterative self-consistent parallel imaging reconstruction from arbitrary k-space." Magnetic resonance in medicine 64.2 (2010): 457-471. (Year: 2010).*

Ulas, Cagdas, et al. "Direct estimation of pharmacokinetic parameters from DCE-MRI using deep CNN with forward physical model loss." Medical Image Computing and Computer Assisted Intervention—MICCAI 2018: 21st International Conference, Granada, Spain, Sep. 16-20, 2018, Proceedings, Part I. (Year: 2018).*

* cited by examiner

SCAN-SPECIFIC RECURRENT NEURAL NETWORK FOR IMAGE RECONSTRUCTION

CROSS-REFERENCE TO RELATED APPLICATION

This application claims priority to and the benefit of U.S. Provisional Patent Application No. 62/879,982 titled "SCAN-SPECIFIC RECURRENT NEURAL NETWORK FOR IMAGE RECONSTRUCTION," filed on Jul. 29, 2019, and the entirety of which is hereby incorporated by reference herein.

STATEMENT REGARDING GOVERNMENT RIGHTS

This invention was made with Government support under Government Contract Nos. R21-EB022951, R01-MH116173, R01-NS074980, R01-NS089212 and R33-CA225400 awarded by the National Institute of Health (NIH) and Government Contract No. CCF-1350563 awarded by the National Science Foundation (NSF). The Government has certain rights in this invention.

BACKGROUND

1. Field

This specification relates to a system, apparatus and/or method for generating a scan-specific neural network for magnetic-resonance imaging (MRI) reconstruction.

2. Description of the Related Art

Slow data acquisition speed has always been an impediment to magnetic resonance imaging (MRI), and developing new methods to improve acquisition speed has been a focus of research for decades. Since the experiment duration for MRI is proportional to the amount of collected data samples, computation imaging methods that can reconstruct high-quality images from incomplete/low quality datasets has been a focus in the field.

One way to achieve faster data acquisition is to sample k-space data below the Nyquist rate, and then use constraints and advanced reconstruction methods to compensate for missing information. Some methods include parallel imaging and phase-constrained, sparsity-constrained, and rank-constrained image reconstruction methods.

Due to modern developments in machine learning, big-data from multiple subjects may be used to train MRI image reconstruction procedures to increase the speed of data acquisition to improve the reconstruction of higher-quality MRI images. Big-data methods are designed to have good generalization capabilities (i.e., the trained reconstruction method can be applied to new data that it was not specifically trained for). These big-data methods, however, depend critically on the availability of a large database of similar data.

Small-data methods, however, are designed with the opposite objective in mind and are tailored to address imaging subjects with uncommon features (e.g., patients with rare pathological conditions) or to reconstruct data that was acquired with novel experimental paradigms for which no previous data may exist. These small-data methods train a different reconstruction procedure for each new dataset, relying on a small amount of scan-specific training data to tailor the reconstruction procedure to the unique characteristics of each image. This approach is possible because: (1) a small amount of fully-sampled scan-specific training data can often be acquired fairly quickly with MRI; and (2) Fourier MRI data (also called "k-space data") often possesses a simple shift-invariant autoregressive structure that can be represented using simple models with a small number of degrees of freedom.

Accordingly, there is a need for a system, an apparatus, a method and/or a device to determine missing data in under-sampled datasets based on the values of neighboring measured data without the need for large amounts data from multiple subjects.

SUMMARY

In general, one aspect of the subject matter described in this specification is embodied in a device, a system and/or an apparatus for generating a high-quality MRI image from data that is limited in quantity or quality. The image reconstruction system includes a memory. The memory is configured to store multiple samples of biological, physiological, neurological or anatomical data with missing or corrupted samples and a deep learning model or neural network. The image reconstruction system includes a processor coupled to the memory. The processor is configured to obtain the multiple samples of k-space data and use these samples to train the parameters of the deep learning model or neural network. The processor is configured to determine the missing or corrupted k-space data using the multiple samples and the deep learning model or neural network. The processor is configured to reconstruct an MRI image using the multiple samples and the k-space data.

These and other embodiments may optionally include one or more of the following features. The deep learning model or neural network may use at least one non-linear activation function. The deep learning model or neural network may be a recurrent neural network (RNN) that may apply the same network layer multiple times. The non-linear activation function may be a rectified linear unit (ReLU) non-linear activation function. The processor may be configured to perform one or more convolutions on the multiple samples to project the missing or corrupted k-space data. The processor may be configured to apply the non-linear activation function while performing the one or more convolutions. The processor may be configured to iterate between performing the one or more convolutions and applying the non-linear activation function a number of times to project or generate one or more missing or corrupted k-space samples. The number of times may be pre-configured or user-inputted.

The k-space data may include one or more missing or corrupted samples. The processor may be configured to interpolate or extrapolate the missing or corrupted k-space data or a linear or nonlinear transformation of the multiple samples using one or more convolutions and at least one of a non-linear activation function or a linear activation function to project or generate the one or more missing or corrupted samples.

The processor may be configured to determine the missing or corrupted k-space data to reconstruct the MRI image for different patterns of under-sampled MRI data. The image reconstruction may include a display. The display may be configured to display the reconstructed MRI image. The processor may be configured to provide the reconstructed MRI image to the display. The multiple samples may be obtained in the Fourier transform domain. The processor may perform an inverse of the Fourier transform domain to reconstruct the MRI image. The number of samples may be less than the Nyquist rate.

In another aspect, the subject matter is embodied in an image reconstruction system. The image reconstruction system includes a memory. The memory is configured to store multiple samples of biological, physiological, neurological or anatomical data that includes missing or corrupted k-space samples and multiple deep learning or neural network models including a first model and a second model. The image reconstruction system includes a processor. The processor is coupled to the memory and configured to train parameters of the first model and the second model using a subset of the k-space data that is complete. The processor is configured to determine a first set of reconstructed k-space data based on the multiple samples that are under-sampled and the first model. The processor is configured to determine a second set of reconstructed k-space data based on the multiple samples that are under-sampled and the second model. The processor is configured to reconstruct a magnetic resonance imaging (MRI) image based on the first set and the second set of reconstructed k-space data.

In another aspect, the subject matter is embodied in a method of generating a magnetic resonance imaging (MRI) image. The method includes obtaining multiple samples that are under-sampled or corrupted. The method includes determining missing or corrupted k-space data using the multiple samples and the deep learning model or neural network. The method includes reconstructing the MRI image using the multiple samples and the missing or corrupted k-space data.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale and may be exaggerated to better illustrate the important features of the present invention. In the drawings, like reference numerals designate like parts throughout the different views.

DETAILED DESCRIPTION

Disclosed herein are systems, apparatuses, devices and methods for an image reconstruction system. The image reconstruction system obtains under-sampled or corrupted Magnetic Resonance Imaging (MRI) data. The MRI data may include biological, physiological, neurological or anatomical data (hereinafter, may be referred to as "health data"). The image reconstruction system uses a deep learning model or neural network to determine the missing or corrupted k-space data to reconstruct an MRI image. By reconstructing the MRI image from under-sampled or corrupted data, the image reconstruction system does not need large amounts of data, such as a large amount of k-space data from the subject being imaged or a database of reference data obtained from other MRI scan subjects, to produce a high-quality MRI image from MRI data that has limited quality or limited quantity. This allows the image reconstruction system to acquire data faster, since less data is necessary, to produce the high-quality MRI image, which improves the efficiency, comfort, and cost-effectiveness of the MRI process.

Other benefits and advantages include an iterative and convolutional process that provides a feedback loop. The iterative and convolutional process allows for a wide range of sampling patterns. Moreover, the deep learning model or neural network is trained directly for each subject using the MRI data with missing or corrupted k-space samples, which minimizes the need for a database of reference MRI data obtained from other MRI scan subjects.

Additionally, the image reconstruction system may include multiple deep learning models or neural network or other models. The use of multiple models may improve the quality samples or may allow the quality of the image to be maintained when using a reduced number and quality of samples.

Figure 1:
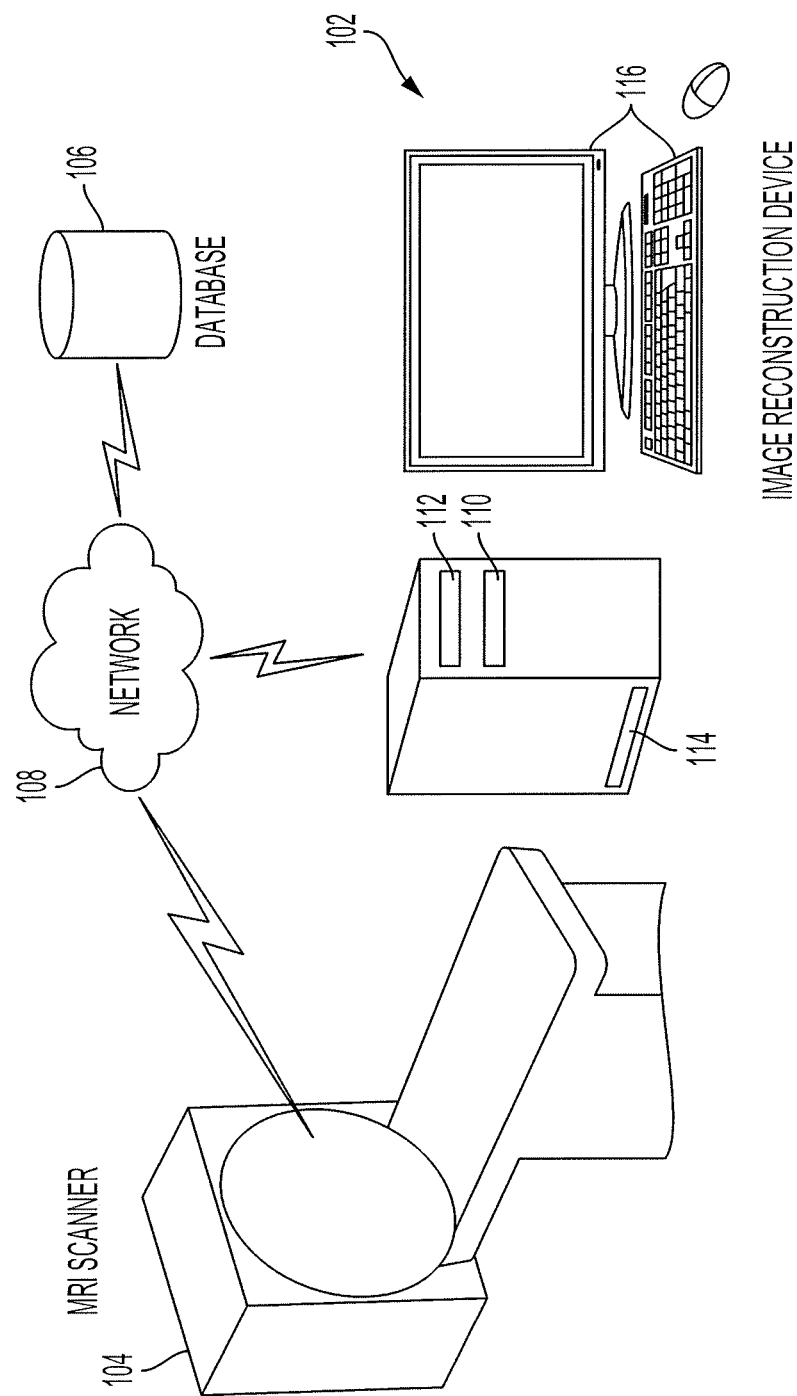
FIG. 1 is a diagram of an example image reconstruction system according to an aspect of the invention.

FIG. 1 shows a diagram of the image reconstruction system 100. The image reconstruction system 100 uses a scan-specific recurrent neural network to perform MRI image reconstruction. The image reconstruction system 100 may use a deep learning model or network features to recover missing or corrupted samples from MRI data. The deep learning model or neural network is trained using autocalibration (ACS) data, which is a subset of the MRI data that does not have missing samples. The deep learning model includes one or more blocks that are iterative and convolutional and take the form of a convolutional autocalibrated scan-specific recurrent neural networks (RNNs). This allows the architecture to admit a wide range of sampling patterns.

The deep learning model trains autocalibrated scan-specific RNN to recover missing or corrupted Fourier ("k-space") data and is a shift-invariant nonlinear autoregressive autocalibrated (AA) deep learning approach for MRI reconstruction. The deep learning model combines a nonlinear deep learning approach with additional constraints and iterative convolutional characteristics. The deep learning model may include an unfolded iterative structure combined with an artificial neural network, which results in a convolutional recurrent neural network (RNN) architecture, which is different than a typical scan-specific feedforward convolutional neural network (CNN) that performs autoregressive k-space interpolation.

Autoregressive MRI reconstruction approaches assume that, for a given channel l and a given k-space sampling position k, the data sample at that position can be accurately represented as a simple shift-invariant function of neighboring data samples from all channels. This autoregressive relationship can be expressed through the general form $$\tilde{\rho}_\ell[k] \approx f_{\ell,\theta}(\{\tilde{\rho}_m[k-k_j]: m \in \{1, \ldots, L\} \text{ and } k_j \in \Delta\})$$
for $\forall k \in \mathbb{Z}^N$.

In the above, $f_{l,\theta}(\cdot)$ is the shift-invariant autoregressive function for channel l that depends on learned parameters $\theta$ and $\Delta$, which defines a local neighborhood system of k-space locations. For example, $\Delta$ can be chosen as:

$$\{k \in \mathbb{Z}^N: 0 < \|k\|_\infty \leq R\}$$

or $$\Delta = \{k \in \mathbb{Z}^N: 0 < \|k\|_2 \leq R\}$$

for some neighborhood radius R.

The shift-invariant autoregressive function may be chosen to have a simple form so that they can be learned from a small amount of training data. For example, the shift-invariant autoregressive function, where the set of $h_m[k_j]$ coefficients correspond to the autoregression parameter $\theta$ may be a simple linear predictive model, $$\tilde{\rho}_\ell[k] = \sum_{m=1}^{L} \sum_{k_j \in \Delta} h_m[k_j] \tilde{\rho}_m[k - k_j] \text{ for } \forall k \in \mathbb{Z}^N.$$

The deep learning model is trained to be scan-specific (i.e., the network is trained specifically to reconstruct one specific dataset, and the trained network is not expected to generalize other scans) based on a small amount of ACS data, and thus, "Big-Data" is not required, alleviating one of the main drawbacks of most other deep learning methods. Moreover, the deep learning model is compatible with a wide range of autocalibrated Cartesian k-space sampling patterns, which provides advantages over models, such as Autocalibrated LORAKS (AC-LORAKS) and RAKI, and can accommodate various sampling strategies.

The image reconstruction system 100 includes an image reconstruction device 102. The image reconstruction system 100 may include an Magnetic Resonance Imaging (MRI) scanner 104 and/or a database 106. The image reconstruction system 100 may include a network 108. The various components of the image reconstruction system 100 may be coupled to or integrated with one another by the network 108. The network 108 may be a wired or a wireless connection, such as a local area network (LAN), a wide area network (WAN), a cellular network, a digital short-range communication (DSRC), the Internet, or a combination thereof, which connects the database 106, the MRI scanner 104 and/or the image reconstruction device 102.

The image reconstruction system 100 may include the MRI scanner 104. The MRI scanner 104 is a large tube that contains power magnets. The MRI scanner 104 may be used to examine a part of the human body to help diagnose conditions, plan treatments and assess the efficacy of a previous treatment. The MRI scanner 104 may provide the image reconstruction device 102 with k-space that missing or corrupted samples, such as corruption by thermal noise. The image reconstruction device 102 extrapolates, interpolates, or otherwise restores the missing or corrupted k-space information and then reconstructions an MRI image that may provide information about the human body, such as biological, physiological, neurological or anatomical data.

The image reconstruction system 100 may include a database 106. A database is any collection of pieces of information that is organized for search and retrieval, such as by a computer, and the database 106 may be organized in tables, schemas, queries, report, or any other data structures. A database may use any number of database management systems. A database 106 may include a third-party server or website that stores or provides information. The information may include real-time information, periodically updated information, or user-inputted information. The information may include health information, such as the biological, physiological, neurological or anatomical data. The data may be under-sampled and contain missing or corrupted k-space data, which may be provided to the image reconstruction device 102.

The image reconstruction system 100 includes an image reconstruction device 102. The image reconstruction device 102 includes a processor 110, a memory 112, network access device 114 and/or a user interface 116. The processor 110 may be a single processor or multiple processors. The processor 110 may be electrically coupled to some or all of the components of the image reconstruction device 102. The processor 110 may be coupled to the memory 112. The processor 110 may obtain input data, such as the samples of the under-sampled or corrupted k-space data and the one or more models, such as a deep learning model or neural network, and use the one or more models and the samples to reconstruct the MRI image. The number of samples in an under-sampled data may be less than the Nyquist rate. The processor 110 may generate or determine the missing or corrupted k-space data from the samples and reconstruct the MRI image. The processor 110 may be used to alert the operator or user of certain conditions and/or to provide the MRI image to the operator once the MRI image is reconstructed.

The memory 112 is coupled to the processor 110. The memory 112 may store instructions to execute on the processor 110. The memory 112 may include one or more of a Random Access Memory (RAM) or other volatile or non-volatile memory. The memory 112 may be a non-transitory memory or a data storage device, such as a hard disk drive, a solid-state disk drive, a hybrid disk drive, or other appropriate data storage, and may further store machine-readable instructions, which may be loaded and executed by the processor 110. The memory 112 may store the samples of the under-sampled data of the health data and/or the one or more models.

The image reconstruction device 102 may include a network access device 114. The network access device 114 may be used to couple the various components of the image reconstruction system 100 via the network 108. The network access device 114 may include a communication port or channel, such as one or more of a Wi-Fi unit, a Bluetooth® unit, a Radio Frequency Identification (RFID) tag or reader, a DSRC unit, or a cellular network unit for accessing a cellular network (such as 3G, 4G or 5G). The network access device 114 may transmit data to and receive data from the various components.

The image reconstruction device 102 may include a user interface 116. The user interface 116 may be part of the image reconstruction device 102 and may include an input device that receives user input from a user interface element, a button, a dial, a microphone, a keyboard, or a touch screen. The user interface 116 may include a touch-screen display or other interface for a user to provide user input to indicate locations of stopping events, home events, terrain events or one or more other charging events. Moreover, the user interface 116 may provide an output device, such as a printer, a display, a speaker, an audio and/or visual indicator, or a refreshable braille display. The user interface 116 may provide the output device, such as a display, any notifications, warnings or alerts and/or provide the generated reconstructed MRI image to an operator or other user.

Figure 2:
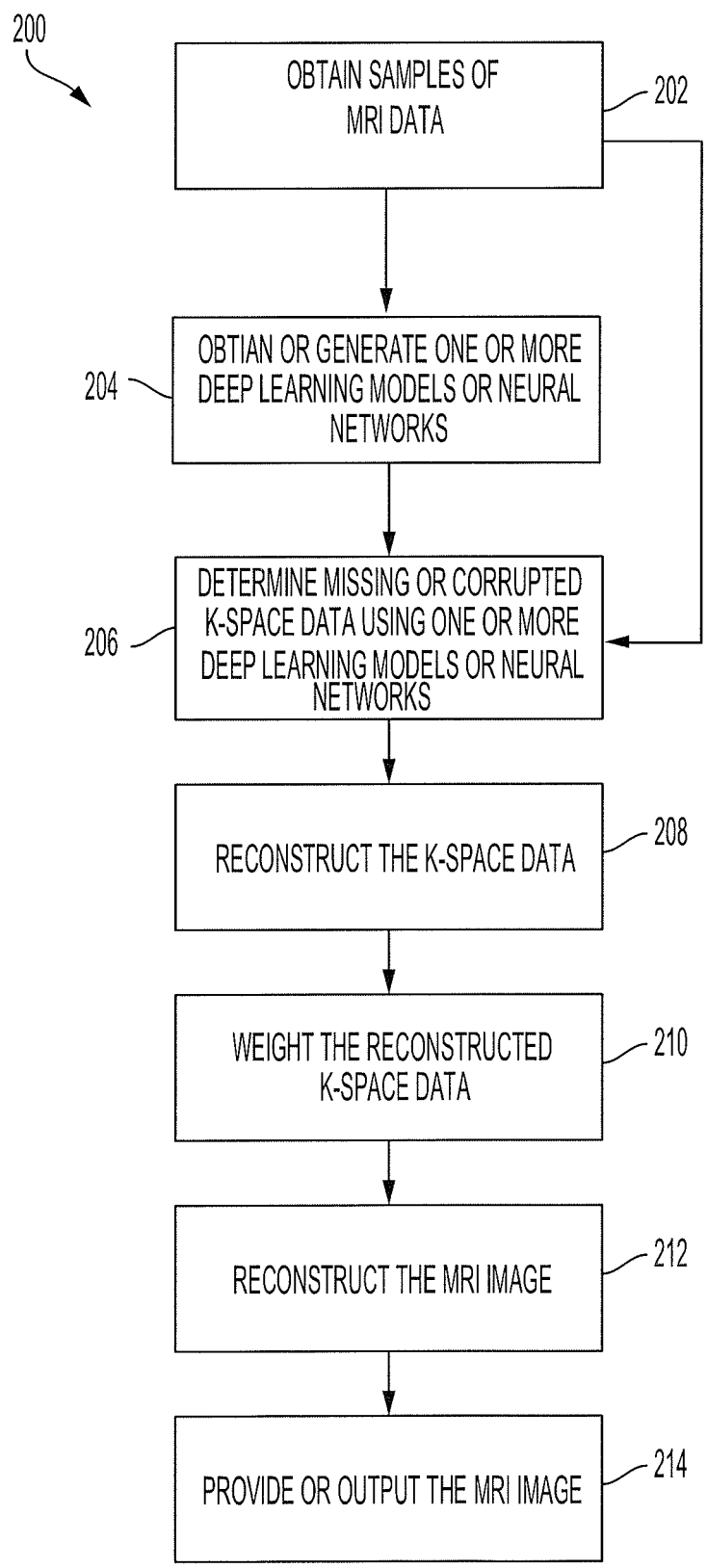
FIG. 2 is a flow diagram of an example process for outputting a high-quality MRI image from under-sampled data using the image reconstruction system of FIG. 1 according to an aspect of the invention.

FIG. 2 is a flow diagram of an example process 200 for outputting a high-quality MRI image from under-sampled or corrupted MRI k-space data. One or more computers or one or more data processing apparatuses, for example, the processor 110 of the image reconstruction system 100 of FIG. 1, appropriately programmed, may implement the process 200.

The image reconstruction system 100 may obtain one or more samples of the MRI k-space data (202). The image reconstruction system 100 may use a single source, such as an image from the MRI scanner 104, as the under-sampled k-space data of the health data to provide to the image reconstruction device 102. The MRI k-space data may contain artifacts or corruption.

Figure 3:
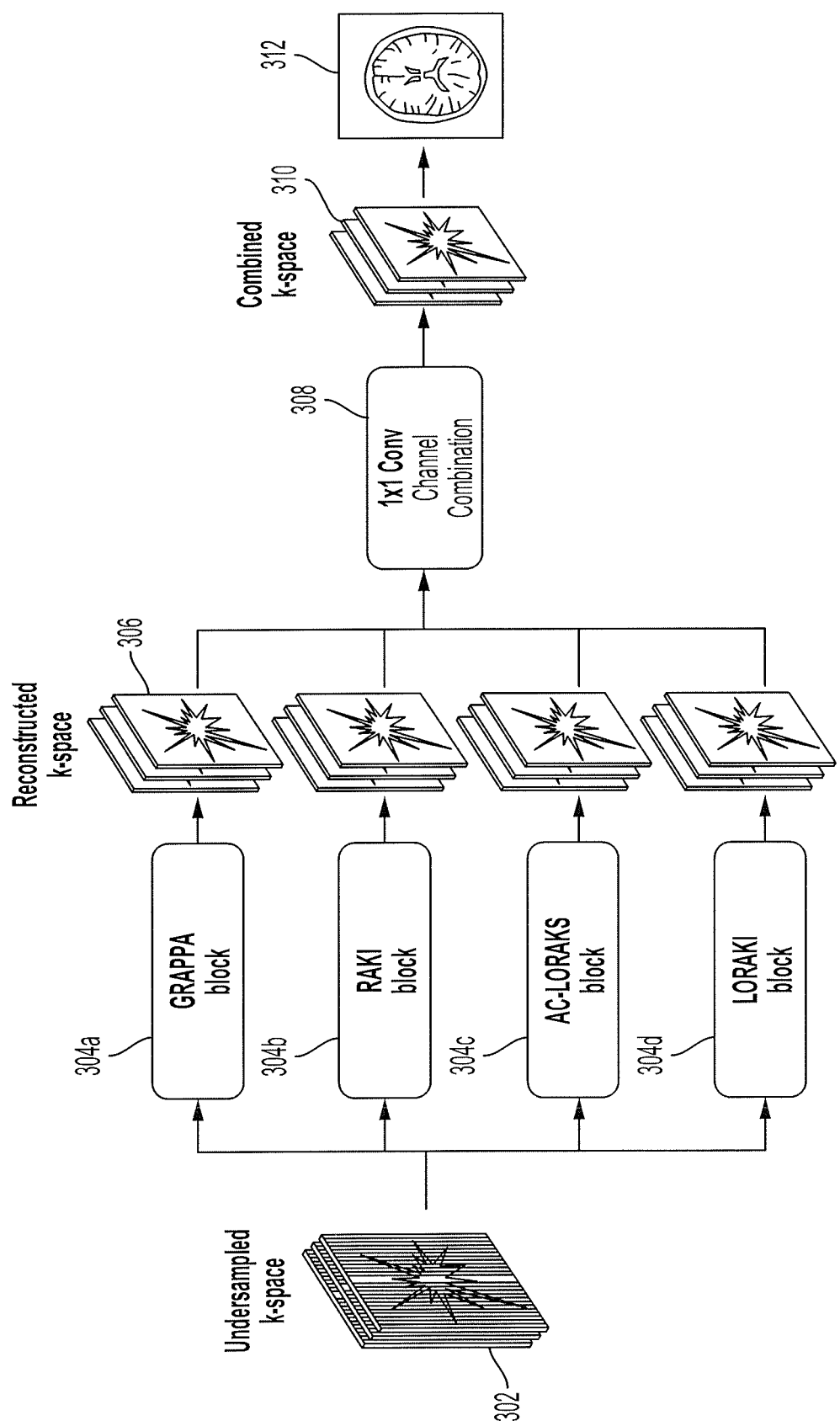
FIG. 3 shows the process for using an ensemble of models to output the high-quality MRI image from the under-sampled data using the image reconstruction system of FIG. 1 according to an aspect of the invention.
Figure 14:
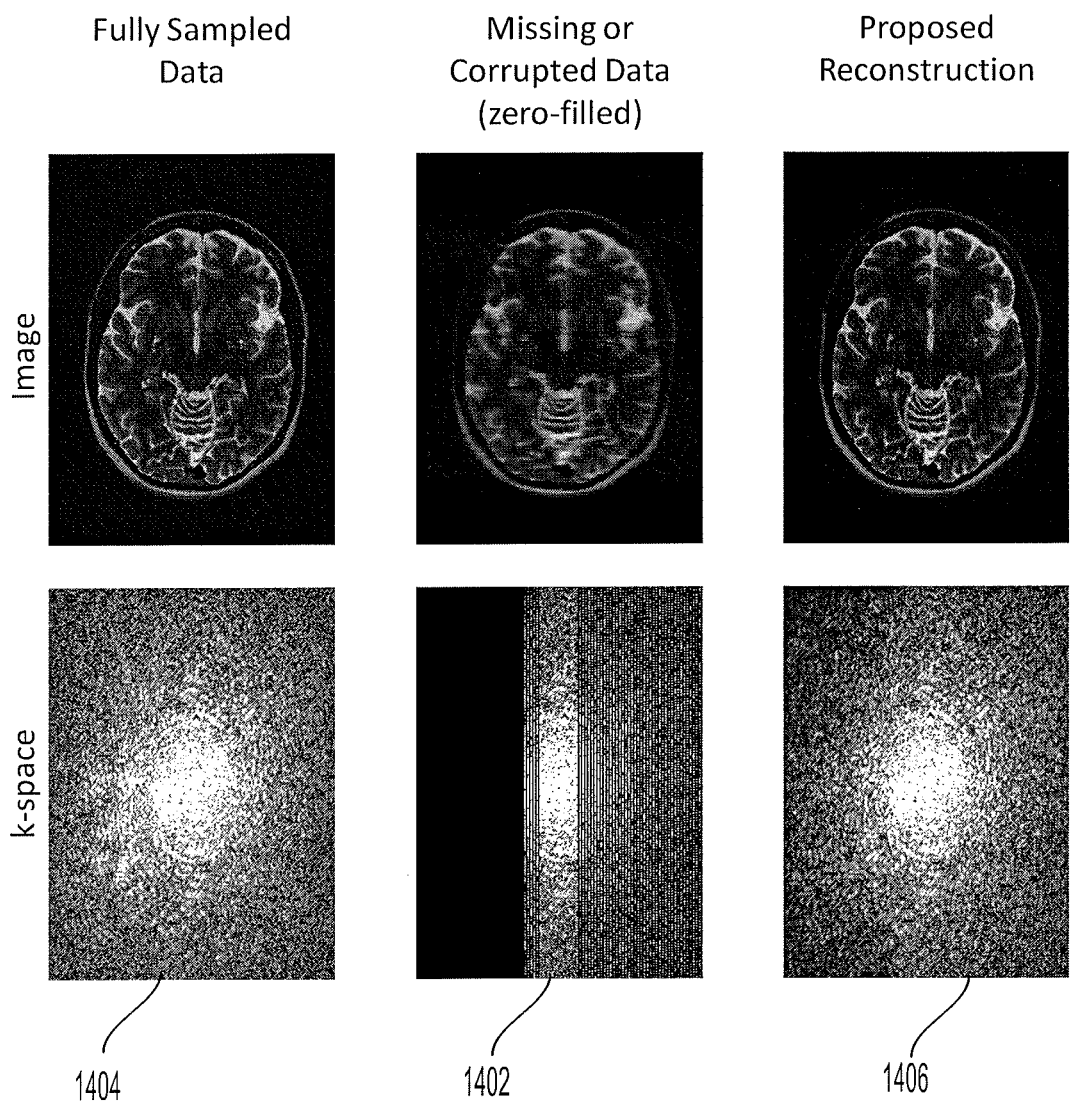
FIG. 14 shows an example image of the k-space data and corresponding image reconstructed using the image reconstruction system of FIG. 1 according to an aspect of the invention.

The image reconstruction device 102 may obtain the one or more samples in the Fourier transform domain. The MRI k-space data is the two-dimensional (2D) or three-dimensional (3D) Fourier transform of the MRI image that is measured. Often the k-space refers to the electromagnetic MRI signal that is digitized and stored during data acquisition, prior to the formation of an MRI image. The k-space data may be under-sampled, such as the under-sampled k-space data 302, as shown in FIG. 3, and the image of the under-sampled or corrupted k-space data 1402, as shown in FIG. 14 for example. The under-sampled or corrupted k-space data may not be fully sampled, e.g., the image of the fully-sampled k-space data 1404, which provides the full final image, and thus, there are missing or corrupted samples of the k-space data within the under-sampled or corrupted k-space data. FIG. 3 illustrates a diagram 300 of the reconstruction of a high-quality MRI image 312, and FIG. 14 shows the results of the reconstruction of the high-quality MRI image using different models.

The k-space data may be sampled on a Cartesian integer lattice, and use the integer vector k to denote the coordinates with respect to that lattice For example, in 2D MRI with sampling intervals of $\Delta k_x$, and $\Delta k_y$, the k-space location $(m\Delta k_x, n\Delta k_y)$ would correspond to the integer vector $k=[m, n]^T$.

In some implementations, the image reconstruction device 102 may obtain the one or more samples of the MRI data from the database 106. For example, the image reconstruction device 102 may obtain samples of the MRI data from the MRI scanner. The samples of the MRI data may be incomplete and have missing or corrupted k-space data, and so, the image reconstruction device 102 only requires a small amount of data, such as an MRI image of a specific patient, to reconstruct the high-quality MRI image.

Figure 7:
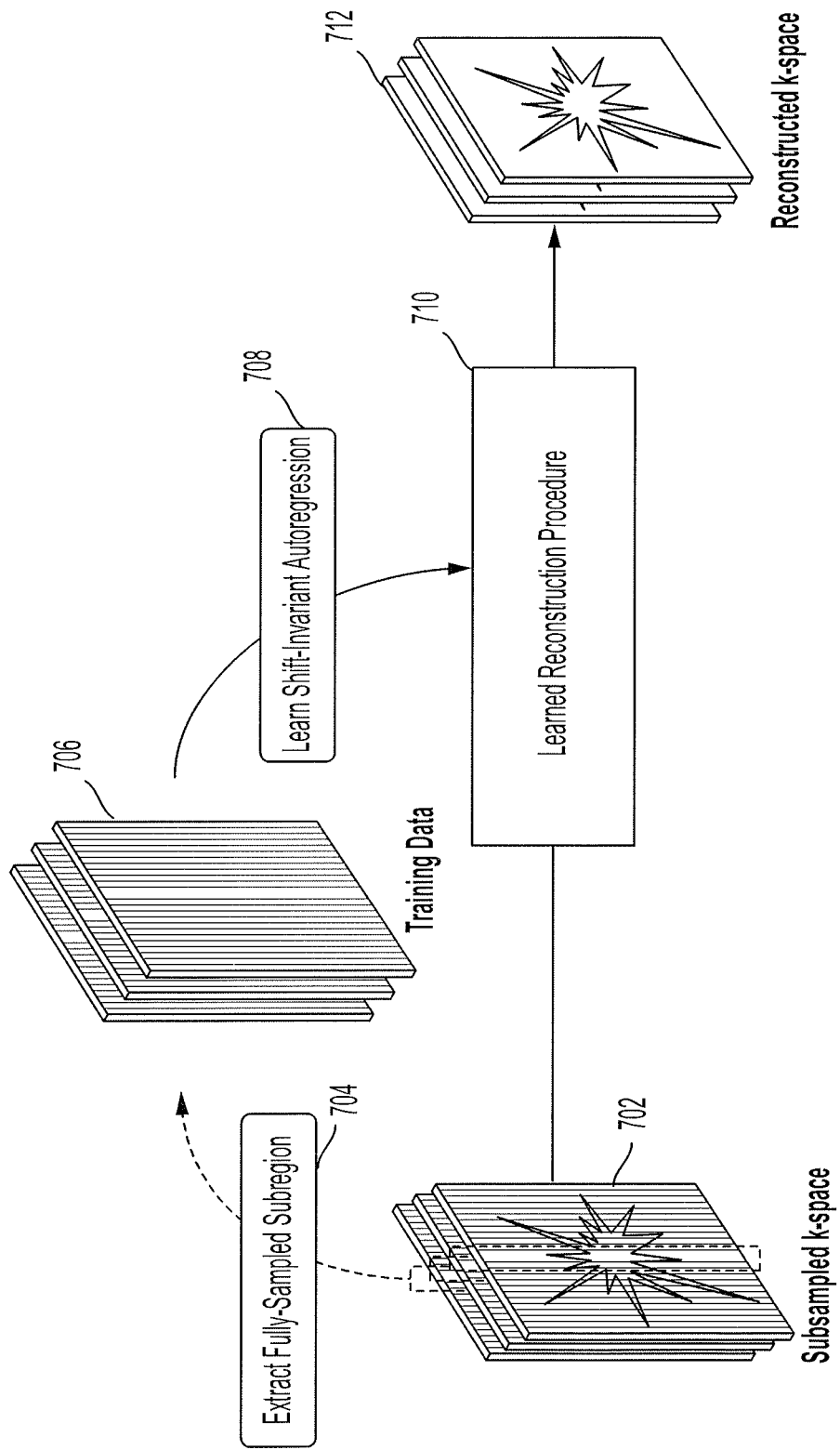
FIG. 7 shows the training procedure of the one or more models using the image reconstruction system of FIG. 1 according to an aspect of the invention.

The image reconstruction system 100 may obtain or generate one or more deep learning models, or neural networks or other models (hereinafter, referred to as "models") 304a-d (204). The image reconstruction system 100 may train the parameters of the deep learning model or neural network using a subset of the k-space data that does not have missing samples. FIG. 7 describes the training procedure of the one or more models.

Figure 4A:
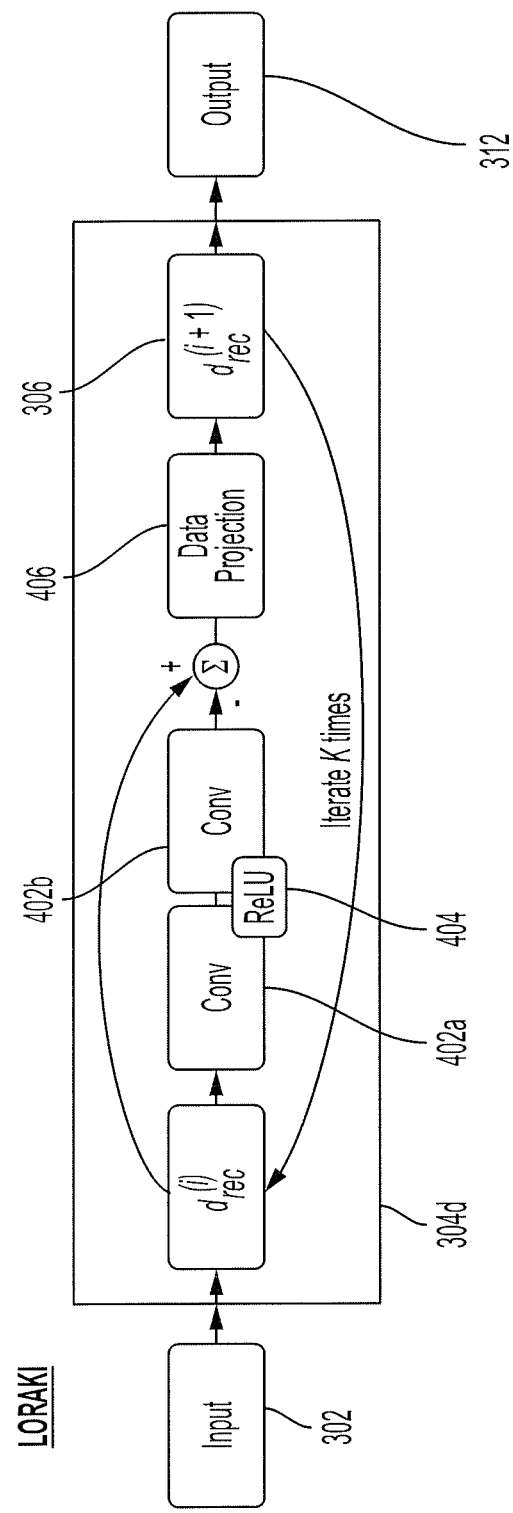
FIG. 4A shows a nonlinear "LORAKI" RNN that may be used by the image reconstruction system of FIG. 1 as one of the deep learning models or neural network blocks of FIG. 2 or FIG. 3 according to an aspect of the invention.

The one or more models 304a-d, such as the model 304d, may include LORAKI. LORAKI is a learning-based image reconstruction model that relies on scan-specific nonlinear autoregressive modeling using a recurrent convolutional neural network, which demonstrates better performance than the previously mentioned models. The LORAKI structure includes nonlinear ReLU activation functions within a convolutional RNN architecture. The LORAKI structure is shown in FIG. 4A for example, and is further described in FIG. 5. Starting from an initialization of $d_{rec}^{(0)}=d_{zp}$, the LORAKI structure iterates the following equation for a total of K iterations. The number of iterations may be user-selected or a pre-configured network parameter, which may be fixed prior to training. The direction may be non-linear in d and may be represented at $g_2((\text{relu}(g_1(d)))$, which implies $$d_{rec}^{(i+1)}=\mathcal{U}(d_{rec}^{(i)}-\lambda g_2(\text{relu}(g_1(d_{rec}^{(i)}))))+d_{zp}.$$

As before, $g_1(\bullet)$ and $g_2(\bullet)$ are convolution layers without bias terms. This new step direction term and the overall iteration is also implicitly associated with some new cost function that imposes consistency with learned nonlinear autoregressive relationships.

The image reconstruction system 100 may obtain a single model to use or multiple models to use to determine the missing k-space data and to reconstruct the k-space data. The image reconstruction system 100 may use an ensemble approach that utilizes multiple models where each model has its own strengths to reconstruct the k-space data. By using multiple models simultaneously as parallel building blocks within a larger data-adaptive reconstruction network, as shown in FIG. 3 for example, the image reconstruction system 100 improves the overall performance of the image reconstruction. Results with real data suggest that the ensemble-based approach can synergistically utilize the strengths of each model, provide robust reconstruction performance without the need for interactive parameter tuning.

In some implementations, the LORAKI structure may make simultaneous use of support, phase, parallel imaging, and sparsity constraints, where the balance between these different constraints is automatically determined through the training procedure.

The one or more models 304a-d, such as the model 304a, may include GRAPPA, which assumes that the exist shift-invariant linear interpolation relationships in k-space such that the value of $d_l[k]$, which is the k-space sample at lattice position k from coil 1, can be accurately predicted as a linear combination of neighboring k-space samples according to $$d_\ell[k] \approx \sum_{c=1}^{L} \sum_{m \in \Lambda_k} \mathcal{W}_{\ell,m,c} d_c[k-m].$$

Figure 4B:
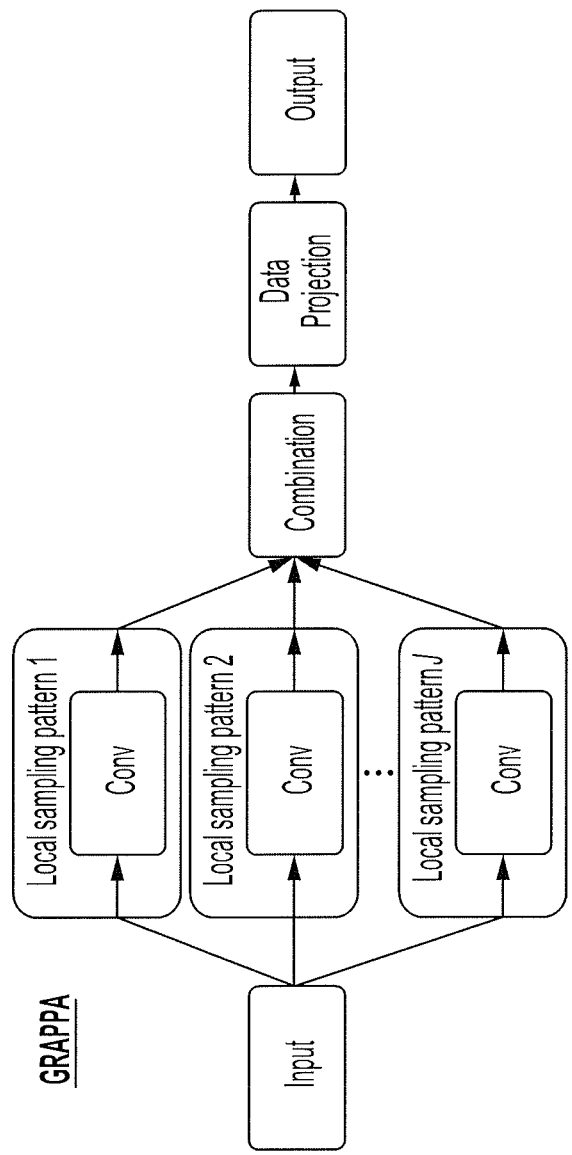
FIG. 4B shows a "GRAPPA" feedforward convolutional neural network (CNN) that may be used by the image reconstruction system of FIG. 1 as one of the deep learning models or neural network blocks of FIG. 2 or FIG. 3 according to an aspect of the invention.

Here, $\Lambda_k$ is the set of integer shift vectors that specify the relative positions of the local neighbors that will be used to interpolate point k, and $w_{l,m,c}$ are the GRAPPA kernel weights. Because GRAPPA assumes this relationship is shift-invariant, it can be represented in convolutional form, and a small amount of ACS data can be used to train the values of the kernel weights. However, a different set of kernel weights needs to be estimated for each distinct configuration of the local sampling neighborhood. GRAPPA is usually applied in scenarios with uniform under sampling, in which case there is a lot of repetition in the local sampling configuration, resulting in only a small number of distinct neighborhood configurations $\Lambda_k$. The structure of the GRAPPA CNN is shown in FIG. 4B, for example.

The one or more models 304a-d, such as the model 304b, may include RAKI. RAKI extends GRAPPA by using multiple convolution layers along with rectified linear unit (ReLU) activation functions. In particular the RAKI network can be represented as $$[d_{rec}]_\ell \approx [d_{zp}]_\ell + \sum_{j=1}^{J} g_j \odot [f_{\ell,3}(\text{relu}(f_{\ell,2}(\text{relu}(f_{\ell,1}(d_{zp}))))))]_j.$$

Figure 4C:
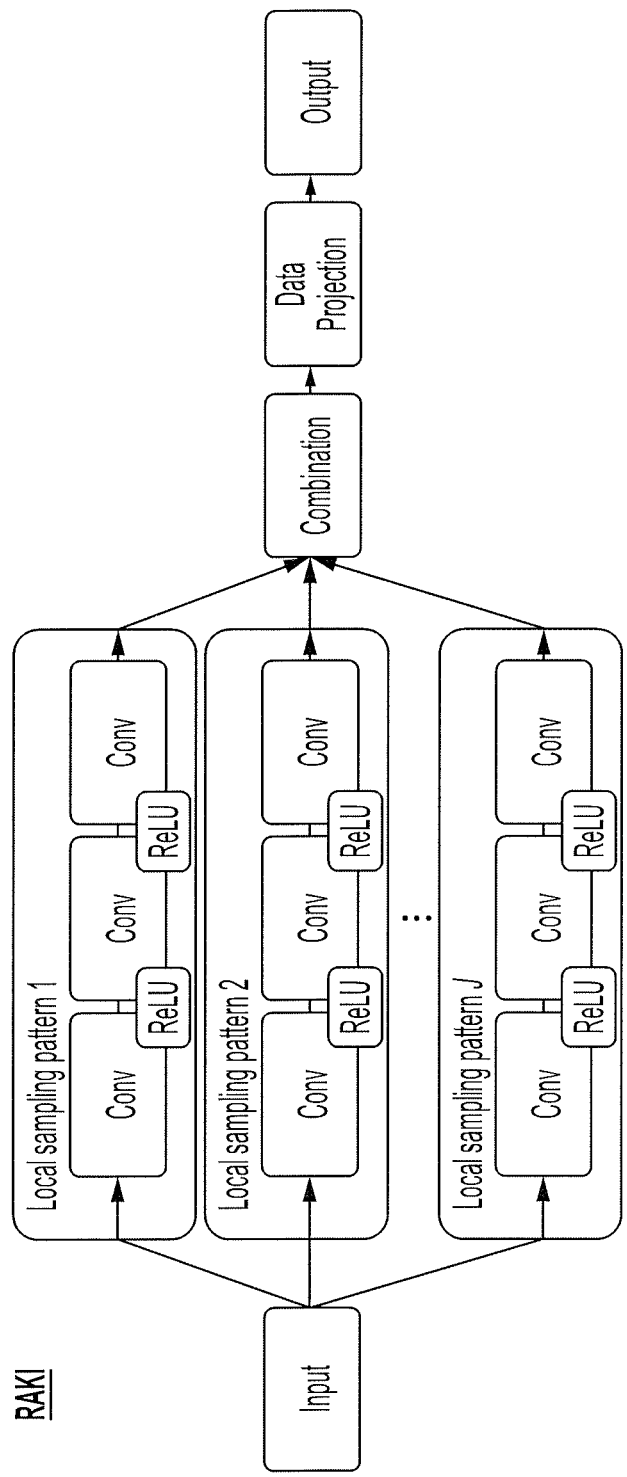
FIG. 4C shows a "RAKI" multi-layer feed forward CNN that may be used by the image reconstruction system of FIG. 1 as one of the deep learning models or neural network blocks of FIG. 2 or FIG. 3 according to an aspect of the invention.

In the above-mentioned function, l=1, . . . , L and $f_{l,1}(\bullet)$, $f_{l,2}(\bullet)$, and $f_{l,3}(\bullet)$, are each linear convolution layers without bias terms, and the ReLU activation function relu(•) is an elementwise operation that outputs a vector with the same size as the input, with the ith element of the output of relu(x) defined as max($x_i$,0). The structure of the RAKI CNN is shown in FIG. 4C, for example.

Figure 4D:
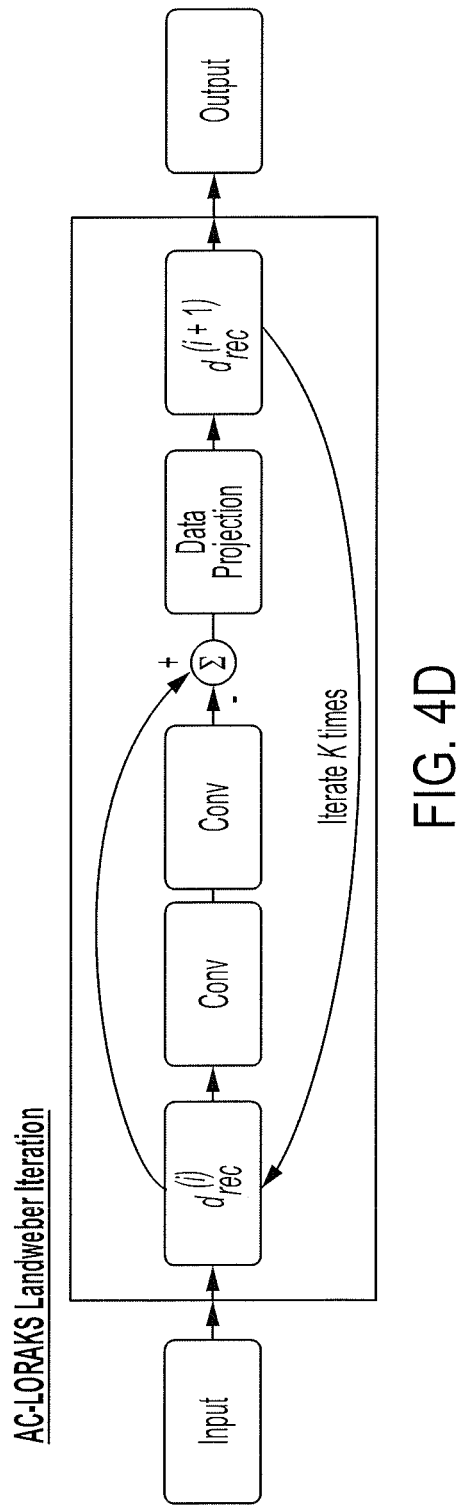
FIG. 4D shows a linear "AC-LORAKS" recurrent neural network (RNN) that may be used by the image reconstruction system of FIG. 1 as one of the deep learning models or neural network blocks of FIG. 2 or FIG. 3 according to an aspect of the invention.

The one or more models 304a-d, such as the model 304c, may include LORAKS or a LORAKS variant, such as AC-LORAKS, which is based on the association between autoregressive k-space structure and a variety of classical image reconstruction constraints (including limited support, smooth phase, sparsity, and parallel imaging constraints). Specifically, LORAKS is based on the observation that when one or more of the classical constraints are satisfied by a given image, then the k-space data will approximately obey at least one linear autoregression relationship, which implies that an appropriately-constructed structure matrix (e.g., convolution-structure Hankel or Toeplitz matrices) formed from the k-space data will have distinct nullspace vectors associated with each linear autoregression relationship. Users of LORAKS do not need to make prior modeling assumptions about the support, phase, or parallel imaging characteristics of the images as all this information is implicitly captured by the nullspace of the structured matrix, which is estimated automatically from the data. A fast linear AA method called AC-LORAKS may be used if ACS data is acquired. The ACS data uses a structured "calibration" matrix, and the nullspace of this calibration matrix is estimated. The nullspace matrix captures linear autoregressive relationships that should hold for all points in k-space, and the fully sampled k-space data can then be reconstructed by finding the missing data points. The AC-LORAKS RNN is shown in FIG. 4D for example.

Figure 5:
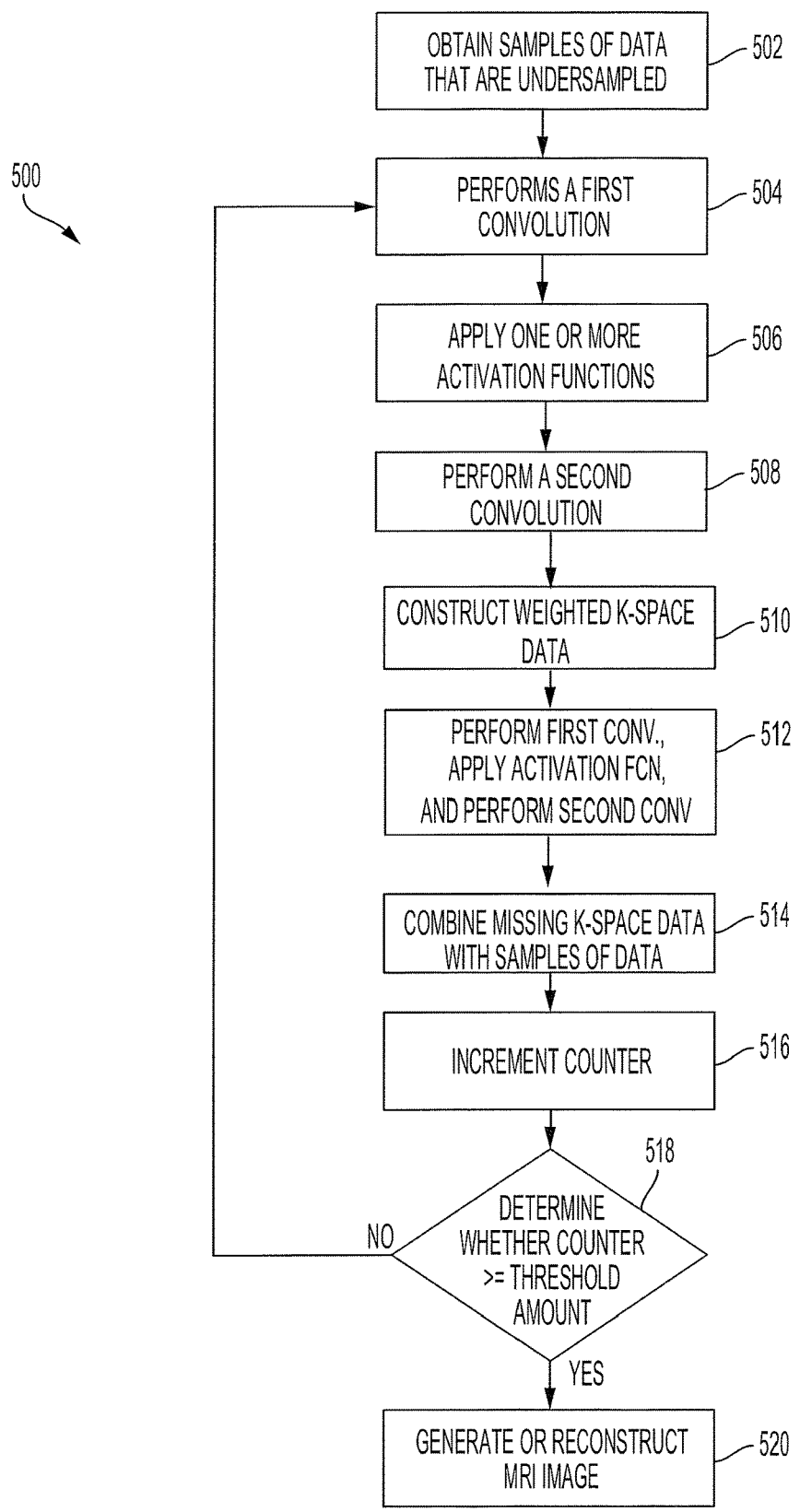
FIG. 5 is a flow diagram of an example process of the image reconstruction system of FIG. 1 using an RNN, such as the LORAKI structure of FIG. 4A, to reconstruct the high-quality MRI image according to an aspect of the invention.

The image reconstruction system 100 determines or generates the missing or corrupted k-space data (206). The image reconstruction system 100 may determine the missing or corrupted k-space data from the samples of the MRI data and using the one or more deep learning models or neural networks or other models. The image reconstruction system 100 uses the one or more models, such as the LORAKI model, which may be an autocalibrated scan-specific recurrent neural network that applies the same network layer multiple times, to determine the missing or corrupted k-space data. The image reconstruction system 100 interpolates or extrapolates the missing or corrupted k-space data by applying the one or more models 304a-d. The image reconstruction system 100 may use any one of the one or more models to interpolate or extrapolate the missing or corrupted k-space data. The one or more models may utilize a linear or nonlinear transformation of the MRI data with the missing or corrupted k-space samples. In some implementations, the image reconstruction system 100 may perform one or more convolutions and/or apply a linear or a nonlinear activation function to generate the missing or corrupted k-space data. FIG. 5 further describes the process for determining the missing or corrupted k-space data.

In some implementations, the image reconstruction system 100 may determine multiple sets of the missing or corrupted k-space data using multiple different models. The image reconstruction system 100 applies different models or different autocalibrated methods and implements them as parallel reconstruction blocks to the under-sampled or corrupted k-space data that is provided in each channel. For example, the image reconstruction system 100 may determine a first set of the missing or corrupted k-space data using the LORAKI model and a second set of the missing or corrupted k-space data using the GRAPPA model. The image reconstruction system 100 may determine any number of sets of the missing or corrupted k-space data using any of the multiple different models, such as the LORAKI, GRAPPA, RAKI and/or AC-LORAKS models. By computing multiple sets of the missing or corrupted k-space data, the image reconstruction system 100 may better interpolate or extrapolate the missing or corrupted k-space data to produce a high-quality reconstructed MRI image.

Once the missing or corrupted k-space data is determined, the image reconstruction system 100 may reconstruct the k-space data (208). The k-space data may be reconstructed for each channel. The image reconstruction system 100 combines the generated or determined missing or corrupted k-space data with the samples of the MRI k-space data that were under-sampled to form the reconstructed k-space data 306, which includes the missing or corrupted k-space data and the sampled data. The image reconstruction system 100 reconstructs various sets of the reconstructed k-space data 306 for each set of the missing or corrupted k-space data that was formed using the various models in the one or more channels. For example, the image 1406 shows the reconstructed k-space data.

When there are multiple channels of reconstructed k-space data 306, due to applying different models 304a-d to the under-sampled k-space data 302, the image reconstruction system 100 may weight each set of reconstructed k-space data 306 (210). The weight for each set of reconstructed k-space data may be pre-configured, user-inputted or dynamic. The image reconstruction system 100 may weight each set of reconstructed k-space data based on an accuracy or an error rate of the corresponding model 304a-d applied to the under-sampled k-space data in the corresponding channel. For example, a greater weight may be assigned to the corresponding set of reconstructed k-space data 306 that was generated using the corresponding model 304a-d with the highest accuracy or least error rate, and similarly, a lesser weight may be assigned to the corresponding set of reconstructed k-space data 306 that was generated using the corresponding model 304a-d with the lowest accuracy or greatest error rate. The image reconstruction system 100 may update the weight dynamically by comparing the reconstructed k-space data 306 to the high-quality MRI image 312 upon completion to determine the accuracy and/or error rate.

Once the image reconstruction system 100 forms the reconstructed k-space data 306, the image reconstruction system 100 reconstructs the MRI image (212). The image reconstruction system 100 may perform a convolution of multiple channels when there are multiple sets of reconstructed k-space data 306 as a result of applying multiple models 304a-d to the under-sampled k-space data 302. This final learned convolutional combination layer 308 combines the multiple sets of reconstructed k-space data 306 into a combined k-space data 310. The final learned convolutional combination layer 308 may be a 1×1 convolutional layer, whose weights are automatically adapted to place more or less emphasis on the results from different blocks depending on their performance. The combined k-space data 310 is a used to generate the high-quality MRI image 312.

Specifically, if $d \in \mathbb{R}^{M \times Q}$ denotes the multi-coil input data (which has been represented as real valued by separating the real and imaginary components of the complex Fourier data samples, the data that has been collected using an array of Q coils) and if $f_i(\bullet, \theta): \mathbb{R}^{M \times Q} \to \mathbb{R}^{N \times Q}$ denotes the reconstruction operator for the ith block with learnable parameters $\theta_i$, then the ensemble-based network performs Fourier data reconstruction according to:

$$[\hat{k}]_q = \sum_i \mathcal{W}_{iq} [f_i(d, \theta_i)]_q \text{ for } q = 1, \ldots, Q.$$

Here, $[\hat{k}]_q$ is the reconstructed (interpolated) Fourier data for the qth coil from the ensemble-based approach, $[f_i(d, \theta_i)]_q$ is the reconstructed Fourier data for the qth coil from the ith block, and $w_{iq}$ is the learned combination weight as used by the 1×1 convolutional layer. The training of the network parameters is performed in an end-to-end manner using the ACS training data, which may be denoted by $k_{ACS}$, and various synthetically-subsampled versions of the ACS data obtained with different subsampling masks, which may be denoted by $d_{ACS}^{(p)}$ for p=1, . . . , P. Specifically, the $w_{iq}$ and $\theta_i$ are obtained by solving the following optimization problem:

$$\min_{\{w_{iq}\},\{\theta_i\}} \sum_{p,q} \lambda \left\| [k_{ACS}]_q - \sum_i \mathcal{W}_{iq} [f_i(d_{ACS}^{(p)}, \theta_i)]_q \right\|^2 + \sum_p \sum_i \left\| k_{ACS} - f_i(d_{ACS}^{(p)}, \theta_i) \right\|_F^2,$$

where the first term in this cost function is a standard mean-squared error (MSE) loss for the overall ensemble network, and the remaining terms constitute MSE loss functions for each of the individual reconstruction blocks. This formulation not only encourages the good reconstruction performance of the ensemble, but is also designed to encourage the good performance of each individual reconstruction block when considered in isolation (which helps to avoid overfitting of the parameters of the ensemble network, which needs to be trained from the same small amount of ACS data that each individual reconstruction block was originally designed to be trained with).

After the one or more sets of reconstructed k-space data 306 are combined, the image reconstruction system 100 generates, provides and outputs the high-quality MRI image 312 (214). The image reconstruction system 100 may perform an inverse of the Fourier transform domain to reconstruct the high-quality MRI image 312 from the reconstructed k-space data 306. The image reconstruction system 100 may display the high-quality MRI image 312 on the user interface 116 to a user or other operator. The reconstructed MRI image using the LORAKI model outperforms and is of higher quality or resolution than the reconstructed MRI images using the other models.

FIG. 5 is a flow diagram of an example process 500 using an autocalibrated scan-specific recurrent neural network, such as LORAKI, to reconstruct the MRI image. One or more computers or one or more data processing apparatuses, for example, the processor 110 of the image reconstruction system 100 of FIG. 1, appropriately programmed, may implement the process 500.

Figure 6:
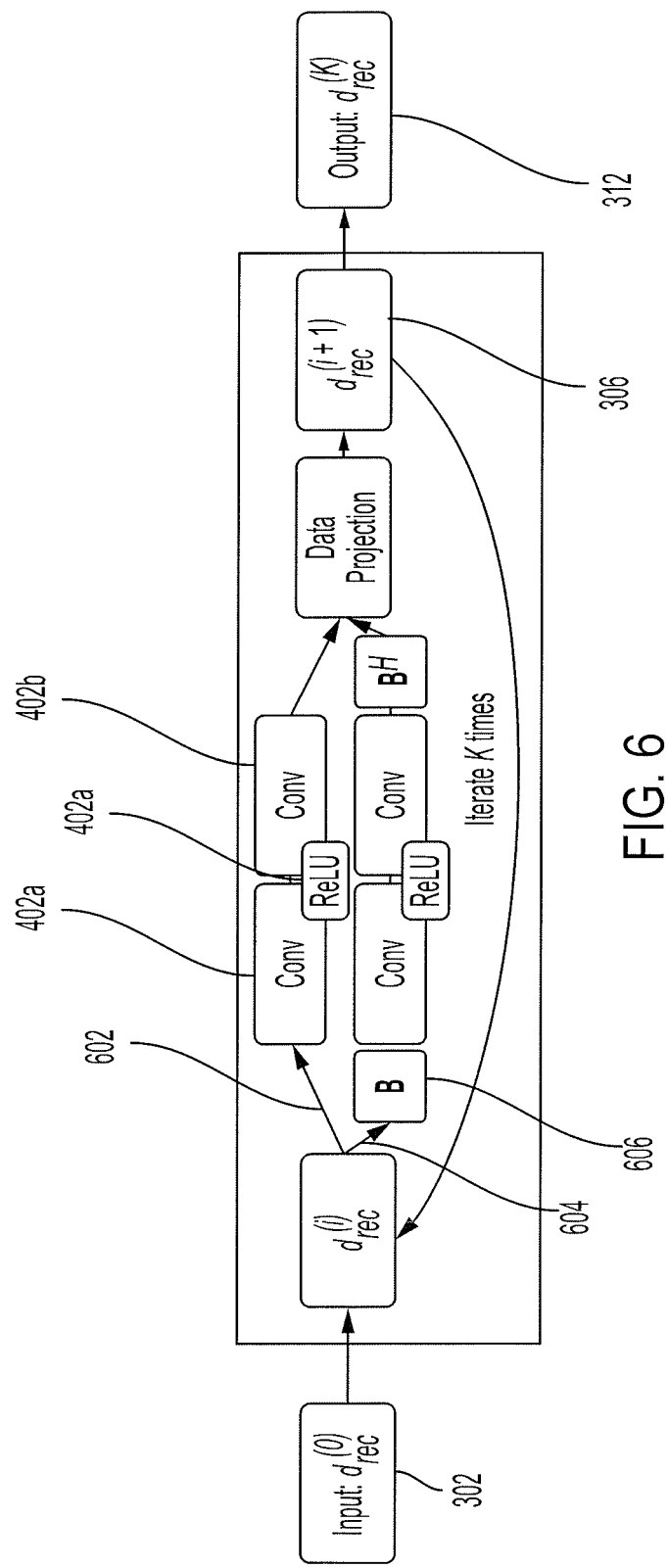
FIG. 6 shows the image reconstruction system of FIG. 1 using a dual constraint LORAKI network structure to reconstruct the high-quality MRI image according to an aspect of the invention.

The image reconstruction system 100 obtains samples of MRI data that are under-sampled or corrupted, as described above (502). Once the samples of the MRI data, e.g., the under-sampled k-space data 302, are obtained the image reconstruction system 100 uses the samples of the MRI data as inputs in the model, which may be an autocalibrated scan-specific RNN. The image reconstruction system 100 may feed the samples of the k-space data through a LORAKI network structure that has a single set of constraints, as shown in FIG. 4A for example, or a LORAKI network structure that is extended to model transform-domain sparsity constraints and has a dual set of constraints to impose the sparsity constraints, as shown in FIG. 6 for example. The dual-constraint LORAKI network structure models the transform-domain sparsity constraints, in addition to the constraints employed the single constraint LORAKI network structure. The dual constraint LORAKI network structure has two paths to model the constraint paths 602, 604.

In a single constraint LORAKI network structure or in a first constraint or path of the dual constraint LORAKI network structure, the image reconstruction system 100 performs a first convolution 402a (504). The image reconstruction system 100 may impose a limited support, smooth phase, and multi-channel correlation constraints. The convolution may be without bias terms. The image reconstruction system 100 may use ellipsoidal convolution kernels instead of rectangular convolution kernels to maintain consistency and improve empirical performance. The $R_1 \times R_2$ ellipsoidal convolution kernel may be viewed as a special case of a standard $R_1 \times R_2$ rectangular kernel, where the values in the corners of the rectangle (i.e., the region outside the ellipse inscribed within the rectangle) are forced to be zero. Ellipsoidal kernels have fewer degrees of freedom to achieve the same special resolution characteristics as rectangular kernels and more isotropic resolution characteristics rather than anisotropic resolution associated with rectangular kernels. Here, the ellipsoidal kernels For example, the image reconstruction system may use ellipsoidal convolution kernels that use $R_1=R_2=5$ for the first convolution 402a and also later the second convolution 402b.

Once the first convolution 402a has been performed or while the one or more convolutions are performed, the image reconstruction system 100 may apply one or more activation functions 404 to the convoluted data (506). The one or more activation functions 404 may be a nonlinear activation function, such as a nonlinear ReLU activation function, within the convolutional RNN architecture, i.e., in between the first convolution and the second convolution. The ReLU activation function may be element wise operation that outputs a vector with the same size as the input. In some implementations, the activation function may be a linear activation function. The convolutions may provide a linear relationship between neighboring samples, and by utilizing the nonlinear function, the image reconstruction system 100 also combines the use of a nonlinear relationship between the neighboring samples.

After the application of the one or more activation functions 404 to the convoluted data, the image reconstruction system 100 performs a second convolution 402b (508). Similar to the performance of the first convolution 402a, the image reconstruction system 100 may perform the second convolution 402b using ellipsoidal convolution kernels. The second convolution 402b may be performed after the application of the activation function 404 to interpolate or extrapolate the missing or corrupted k-space data.

When using a dual constraint LORAKI network structure that models the transform-domain sparsity constraints, the image reconstruction system 100 may simultaneously, concurrently and/or in conjunction with the first constraint path 602 employ a matrix B 606 to construct a weighted k-space data in the second constraint path 604 (510). The weighted k-space data may be represented as $\tilde{w}_l = b[k]\tilde{\rho}_l[k]$, which corresponds to a high-pass filtered image. The image reconstruction system 100 may employ the matrix B to the under-sampled or corrupted k-space data in a second network layer that is in a separate channel or path from the first network layer. This weighted data will possess shift-invariant autoregressive characteristics when the high-pas filtered image has sparsity characteristics. The image reconstruction system 100 weights the k-space data using the matrix B before performing the one or more convolutions and applying the activation function in between the two or more convolutions in the second network layer.

When using the dual constraint LORAKI network structure, the image reconstruction system 100 performs the first convolution 402a, applies the activation function 404, and subsequently performs the second convolution 402b after weighting the k-space data using the matrix B 606 in the second constraint path 604 (512). The second constraint path 604 may impose autoregression-based transform-domain sparsity constraints. These constraints may be implicit in different sets of linear filter coefficients, which can be learned from the nullspace vectors of a structured matrix formed from weighted autocalibration data. The image reconstruction system 100 may perform the one or more convolutions 402a-b and/or the application of the activation function in the second constraint path 604, in a similar manner as that described for the first constraint path 602 and/or a single constraint LORAKI network structure. By weighting, convoluting and applying the activation function to the under-sampled k-space data, the image reconstruction system 100 projects or determines the missing or corrupted k-space data. The projected data 406 forms a part of the reconstructed k-space data. The image reconstruction system 100 interpolates or extrapolates the missing or corrupted k-space data.

The image reconstruction system 100 combines the missing or corrupted k-space data (or "projected data") with the previously obtained samples of MRI k-space data to form the reconstructed k-space data 306 (514). The image reconstruction system 100 may combines the missing or corrupted k-space data from one or more of the network layers with the obtained samples of MRI k-space data to form the reconstructed k-space data. The missing or corrupted k-space data is formed from the convoluted data that has the activation function applied. The convoluted data represents the interpolated or extrapolated data that corresponds to the missing or corrupted k-space data and when combined with the obtained samples form the reconstructed k-space data.

The image reconstruction system 100 increments a counter (516). The counter tracks the number of iterations or times that the health data is fed back through the model, such as the model 304d. The image reconstruction system 100 feeds the reconstructed k-space data back into the model as an input to further train the model and/or improve the reconstruction of the k-space data, and consequently, generate a high-quality MRI image.

The image reconstruction system 100 determines whether the counter is greater than or equal to a threshold amount (518). The threshold amount may be user-configured, user-inputted or a pre-configured number of iterations. The threshold amount indicates the number of iterations that the reconstructed k-space data is fed back through the model as an input to improve the reconstruction of the k-space data to produce or generate the high-quality MRI image. When the counter is less than the threshold amount, the image reconstruction system 100 feeds the reconstructed k-space data back through the model as an input, and thus, form a RNN (504). When the counter is greater than or equal to the threshold amount, the image reconstruction system 100 finishes generating or reconstructing the high-quality MRI image 312 and provides the high-quality MRI image 312 to the user or operator (520). The high-quality MRI image may have a resolution or fidelity that is based on various factors. The factors include the fidelity or resolution of the initial MRI image, the number of iterations through the RNN, and/or other image features, such as smooth phase, empty space or a large number of coils from which the input is received. The image reconstruction system 100 may provide the high-quality MRI image 312 to a display on the user interface 116, which displays the MRI image to the user or operator.

FIG. 7 shows a diagram of the process 700 for training of the autocalibrated scan-specific RNN, such as the LORAKI model, to reconstruct the MRI image. One or more computers or one or more data processing apparatuses, for example, the processor 110 of the image reconstruction system 100 of FIG. 1, appropriately programmed, may implement the process 700.

In order to utilize scan-specific autoregression relationships, the scan-specific RNN must possess scan-specific training data. This may be achieved through autocalibration. Autocalibration refers to acquiring subsampled k-space data such that the sampling pattern contains a fully-sampled subregion that may be used to train autoregressive reconstruction models. Various approaches may make use of nonlinear shift-invariant autoregressive relations and/or linear relationships. For example, GRAPPA uses a single scan-specific linear shift-invariant autoregression relationship. In another example, RAKI uses a nonlinear shift-invariant autoregressive relationship. In particular, RAKI makes use of a shallow multi-layer feedforward convolutional neural network architecture, and relies on nonlinear rectified linear unit (ReLU) activation functions to introduce nonlinearity. In other examples, it has been observed that k-space data is expected to obey multiple distinct linear autoregression relationships at the same time, and that imposing all of these relationships simultaneously could outperform the other approaches that only use one at a time.

The image reconstruction system 100 may obtain a dataset of the k-space data with noise corruption and/or a sub-Nyquist sampling pattern (702). This dataset of the k-space data may include a fully sampled region of k-space data and/or an under-sampled or subsampled region of k-space data. The fully sampled region may also be referred to as ACS data, which may be used to train the one or more models. The LORAKI model is compatible with non-uniform sampling patterns like random sampling or partial Fourier acquisition, and so, there is no need to tailor the reconstruction process to the specific local sampling configurations that are present in the acquired data. This means that when constructing paired fully-sampled and under-sampled training examples, the under-sampling patterns that are used for training do not need to be a close match to the real under-sampling pattern that will be reconstructed.

Once the under-sampled or corrupted k-space data is obtained, the image reconstruction system 100 extracts the fully-sampled subregion of the k-space data (704). The fully-sampled subregion of the k-space data is the autocalibration data that is used to train the model. The image reconstruction system 100 may use the fully-sampled subregion of the k-space data as training data (706). The remaining other under-sampled data is processed using the model by the image reconstruction system 100 to form the reconstructed high-quality MRI image.

The image reconstruction system 100 uses the training data to learn the scan-specific shift-invariant autoregression relationships (708). These autoregressive relationships may hold in k-space whenever the image satisfies limited spatial support, smooth phase, or multi-channel correlation constraints. The image reconstruction system 100 may identify these autoregressive relationships from the nullspace of an appropriately constructed autocalibration matrix. For example, in AC-LORAKS, it can be observed that multiple shift-invariant linear autoregressive relationships hold in k-space and can incorporate the constraints as described as finding a set of Fourier coefficients $\{\tilde{\rho}_l[k]\}$ that minimize:

$$\sum_{p=1}^{P}\sum_{k}\left\|\sum_{k_j\in\Delta}\sum_{\ell=1}^{L}\tilde{\rho}_\ell[k-k_j]\mathcal{V}_{\ell p}[k_j]\right\|_2^2.$$

The multiple shift-invariant linear autoregressive relationships that hold in k-space may be subject to a data consistency constraint that the estimated Fourier coefficient values should match the measured data at every k-space location was actually sampled during data acquisition. This formulation imposes multiple scan-specific linear shift-invariant autoregressive relationships associated with spatial support, smooth support, and multi-channel correlation constraints. The constraints are implicit in the PL different sets of linear coefficients $v_{lp}[k]$, which are learned by computing the nullspace vectors of a structured matrix formed from the autocalibration data.

In another example, the LORAKI model relies on multiple shift-invariant autoregression relationships and makes use of an iterative recurrent neural network architecture. The LORAKI model uses nonlinear ReLU activation functions to enable nonlinear shift-invariant autoregressive modeling to achieve better reconstruction performance. Moreover, the iterative recurrent neural network structure makes LORAKI more compatible with a range of different sampling patterns and a range of different imaging scenarios. Once the shift-invariant autoregression is learned, the image reconstruction system 100 may apply the learned reconstruction procedure to the under-sampled k-space data (710) and form the reconstructed k-space data (712).

Figure 8:
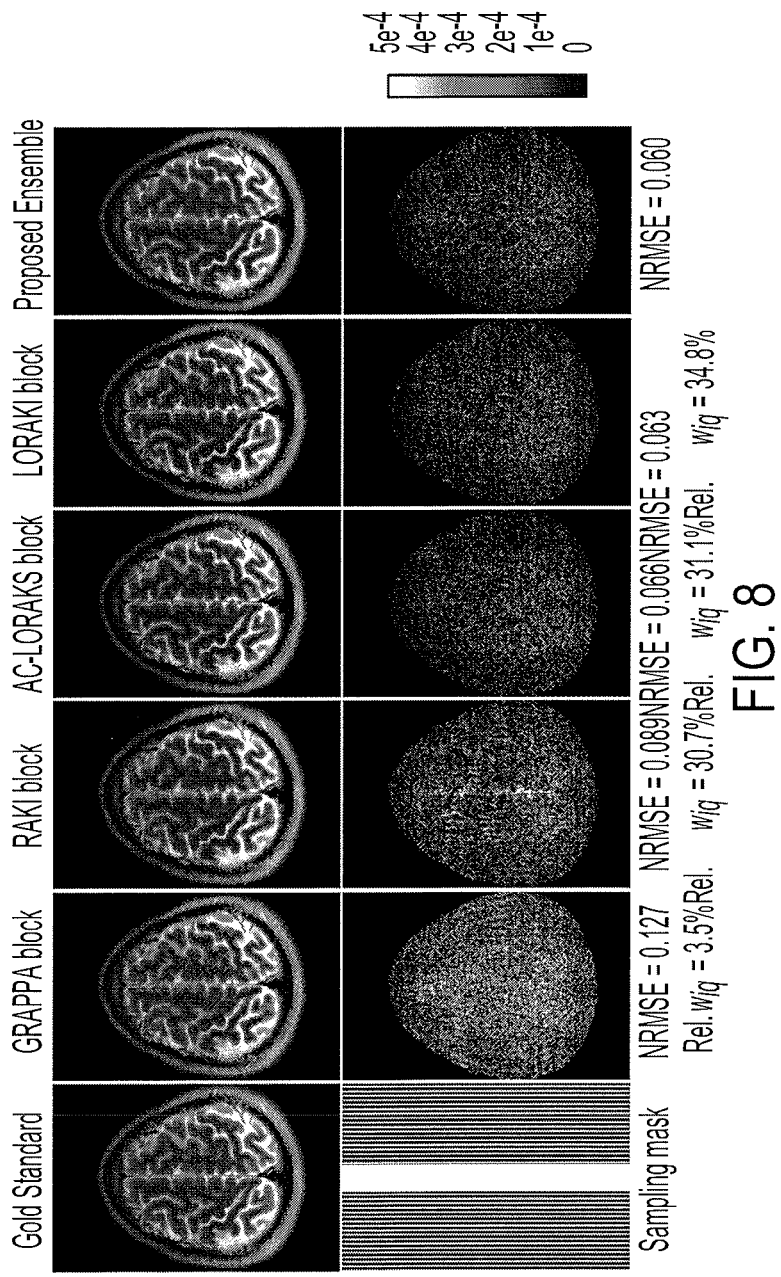
FIG. 8 shows example results of the image reconstruction system of FIG. 1 using the proposed ensemble of models with 4-fold uniform under sampling to reconstruct the high-quality MRI image according to an aspect of the invention.
Figure 9:
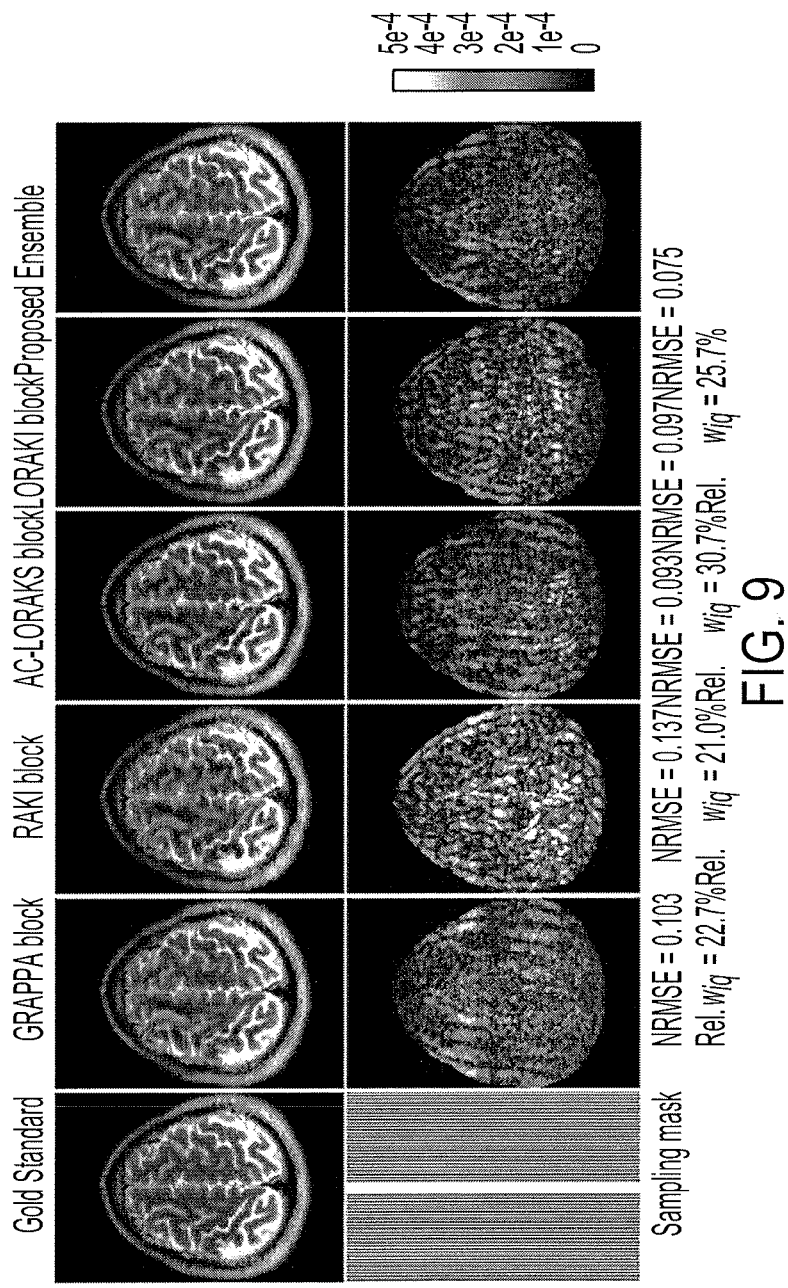
FIG. 9 shows example results of the image reconstruction system of FIG. 1 using the proposed ensemble of models with 3-fold uniform under sampling to reconstruct the high-quality MRI image according to an aspect of the invention.

FIGS. 8-9 shows the results of the image reconstruction system 100 using the proposed ensemble of models to reconstruct the high-quality MRI image. FIG. 8 shows the results from the case with 4-fold uniform under sampling with 24 ACS lines. The top row of images show the coil-combined reconstruction from each block, as well as the final ensemble result. The bottom row shows the corresponding error images. Also shown are the normalized root-mean-squared error (NRMSE) values the relative $w_{i_q}$ value for each block. The performance of the ensemble of models was evaluated using T2-weighted datasets from 5 different subjects.

The quantitative results for the case with 4-fold uniform under sampling with 24 ACS lines is shown below in Table 1. Each cell entry shows the normalized root-mean-squared error (NRMSE) value, with the relative $w_{i_q}$ value for each block shown in parentheses.

TABLE 1

| | GRAPPA block | RAKI block | AC-LORAKS block | LORAKI block | Ensemble |
|---|---|---|---|---|---|
| Subject 1 | 0.127 (3.5%) | 0.089 (30.7%) | 0.066 (31.1%) | 0.063 (34.8%) | 0.000 |
| Subject 2 | 0.120 (2.6%) | 0.089 (33.7%) | 0.065 (28.7%) | 0.062 (35.0%) | 0.000 |
| Subject 3 | 0.167 (10.1%) | 0.109 (27.8%) | 0.076 (29.9%) | 0.072 (32.2%) | 0.071 |
| Subject 4 | 0.148 (0.1%) | 0.098 (12.5%) | 0.078 (28.7%) | 0.074 (58.7%) | 0.070 |
| Subject 5 | 0.168 (0.3%) | 0.112 (11.8%) | 0.082 (41.6%) | 0.076 (46.3%) | 0.074 |

FIG. 9 shows the results from the case with 3-fold uniform under sampling with 8 ACS lines. The top row of images show the coil-combined reconstruction from each block, as well as the final ensemble result. The bottom row of images show the corresponding error images. Also shown are the normalized root-mean-squared error (NRMSE) values and relative $w_{i_q}$ value for each block.

The quantitative results for the case with 3-fold uniform under sampling with 8 ACS lines is shown below in Table 2. Each cell entry shows the NRMSE value and relative $w_{i_q}$ value for each block.

TABLE 3

| | Autocalibrated LORAKS | | | LORAKI | | |
|---|---|---|---|---|---|---|
| Subject # | (SPM) | (T) | (SPM + T) | (SPM) | (T) | (SPM + T) |
| 1 | 0.115 | 0.125 | 0.099 | 0.101 | 0.130 | 0.098 |
| 2 | 0.014 | 0.105 | 0.088 | 0.082 | 0.109 | 0.080 |
| 3 | 0.119 | 0.114 | 0.100 | 0.094 | 0.124 | 0.093 |
| 4 | 0.114 | 0.116 | 0.101 | 0.087 | 0.122 | 0.085 |
| 5 | 0.111 | 0.107 | 0.088 | 0.091 | 0.130 | 0.089 |

TABLE 2

| | GRAPPA block | RAKI block | AC-LORAKS block | LORAKI block | Ensemble |
|---|---|---|---|---|---|
| Subject 1 | 0.103 (22.7%) | 0.137 (21.0%) | 0.093 (30.7%) | 0.097 (25.7%) | 0.075 |
| Subject 2 | 0.139 (2.1%) | 0.132 (14.2%) | 0.084 (38.8%) | 0.101 (44.9%) | 0.081 |
| Subject 3 | 0.194 (4.4%) | 0.189 (14.6%) | 0.115 (50.1%) | 0.125 (21.9%) | 0.104 |
| Subject 4 | 0.136 (19.3%) | 0.165 (24.8%) | 0.114 (19.8%) | 0.122 (36.2%) | 0.103 |
| Subject 5 | 0.187 (7.2%) | 0.168 (27.2%) | 0.131 (36.7%) | 0.136 (29.0%) | 0.118 |

The proposed ensemble-based approach to autocalibrated shift-invariant autoregressive MRI reconstruction employs multiple reconstruction networks simultaneously, which are then adaptively combined together. The results demonstrate that the ensemble can provide excellent performance relative to individual reconstruction methods, and it can adapt automatically in different situations to balance the relative strengths and weaknesses of its constituent reconstruction blocks. The combination may also be synergistic, with the combination of methods being an improvement, and sometimes a substantial improvement, over the best performing individual method.

Figure 10:
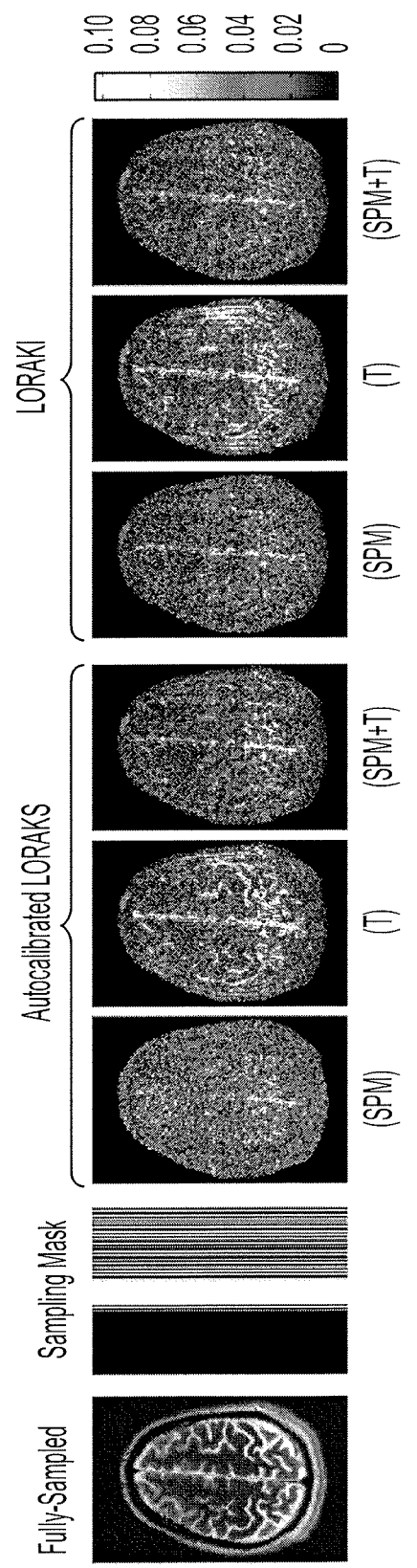
FIG. 10 shows the reconstruction results that compare the use of the LORAKI structure to that of the AC-LORAKS structure by the image reconstruction system of FIG. 1 according to an aspect of the invention.

FIG. 10 shows the reconstruction results for one subject using the LORAKI network structure in comparison to the AC-LORAKS with three different types of autoregressive constraints: (1) limited support, smooth phase, and multi-channel constraints (denoted as SPM); (2) transform-domain sparsity constraints (denoted as T); and (3) the combination of SPM and T constraints. To evaluate the dual constraint LORAKI network structure, a T2-weighted brain MRI data from 5 different subjects was evaluated. Data was acquired with a matrix size of 256×167 with a 12-channel headcoil. Data was retrospectively under-sampled using a partial Fourier sampling pattern with a total effective acceleration factor of 3.8×.

Table 3, shown below, shows the NRMSE values for all five subjects. The results show that the SPM+T works better than using either SPM or TI individually. In addition, LORAKI frequently outperforms AC-LORAKS regardless of the constraints. Unlike AC-LORAKS, the LORAKI network structure may be performed without the manual selection of regularization parameters, which is a nontrivial task and the LORAKI network structure with SPM+T does not require manual tuning of hyperparameters.

FIGS. 11, 12A-12D and 13A-13B show performance measures of various models using T2-weighted data and T1-weighted data. The reconstruction of the MRI image may be performed with subsampled data. Here, the reconstruction of the MRI image using the LORAKI structure, using either synthetic or real ACS data, is compared to the reconstruction using GRAPPA, sRAKI and AC-LORAKS. For simplicity and without loss of generality, the LORAKI structure was implemented using a real-valued deep learning architecture that separates the real and imaginary parts of the data and doubles the effective number of channels. The LORAKI structure is based on the use of the virtual conjugate coil version of LORAKS. In particular, for every original channel, we construct a new virtual channel by applying reversal and complex conjugation operations to the k-space data. This has the effect of further doubling the number of channels effectively leaving 4L channels.

As a result, we have $d_{rec}^{(i)} \in \mathbb{R}^{N_1 \times N_2 \times 4L}$, $g_1(\bullet): \mathbb{R}^{N_1 \times N_2 \times 4L} \to \mathbb{R}^{N_1 \times N_2 \times C}$, and $g_2(\bullet): \mathbb{C}^{N_1 \times N_2 \times C} \to \mathbb{C}^{N_1 \times N_2 \times 4L}$, where C is a user-selected number of intermediate channels. Unless otherwise noted, all of the results use C=64 with K=5 iterations. Moreover, the kernels used are ellipsoidal convolution kernels instead of rectangular convolution kernels.

The reconstruction results were evaluated subjectively using visual inspection, as well as quantitatively using standard normalized root-mean-squared error (NRMSE) and structural similarity index (SSIM) error metrics. For NRMSE, smaller numbers are better with a perfect reconstruction corresponding to an NRMSE value of zero. For SSIM, larger numbers are better with a perfect reconstruction corresponding to an SSIM value of one.

The reconstruction was performed using retrospectively-under-sampled versions of fully-sampled in vivo human brain datasets from two different contexts. In the first case, T2-weighted images from 5 subjects were acquired with 2D Fourier encoding, using a 256×167 acquisition matrix (readout×phase encoding) on a 3T scanner with a 12-channel head coil. For this data, 1 D under sampling simulations were achieved by removing full phase encoding lines from the fully-sampled data. In the other case, T1-weighted images from 5 subjects were acquired with 3D Fourier encoding using an MPRAGE sequence on a 3T scanned with a 12-element multi-channel head coil, which was coil-compressed down to 4 channels. In four cases, this coil-compression was performed in hardware by the scanner itself, while coil-compression was applied. This 3D Fourier data was initially Fourier transformed along the fully-sampled readout direction, resulting in multiple 2D k-space datasets corresponding to different 2D image slices. For this data, 2D under sampling simulations of each slice were achieved by removing individual phase encoding positions.

Figure 11:
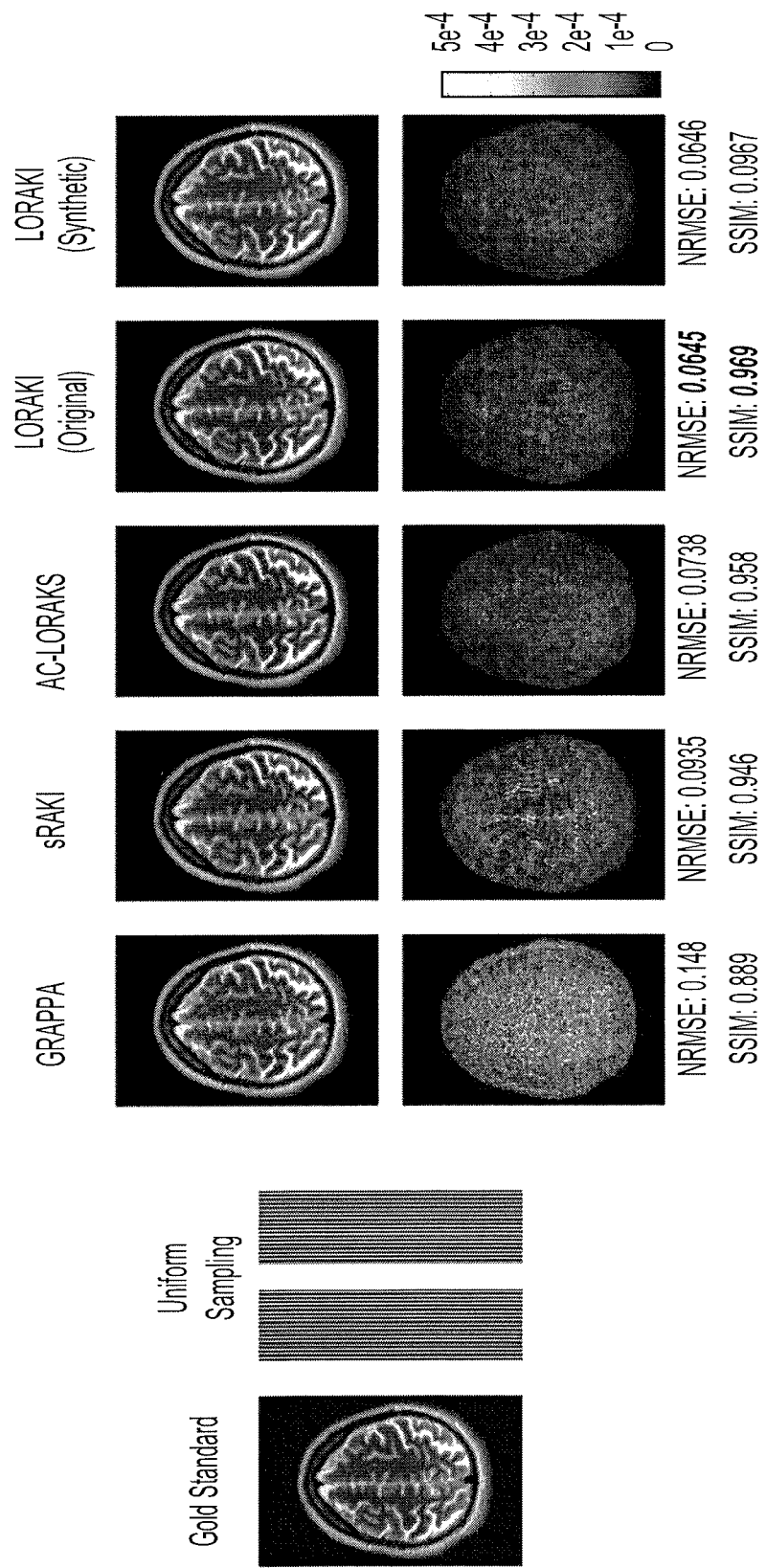
FIG. 11 shows reconstruction results of the use of the LORAKI structure by the image reconstruction system of FIG. 1 according to an aspect of the invention.

FIG. 11 shows representative reconstruction results for uniformly-under-sampled T2-weighted data. The top row shows reconstructed images for one slice in a linear gray-scale, where the gold standard image has been normalized to range form 0 (black) to 1 (white). The bottom row shows error images with the indicated color scale. NRMSE and SSIM values are also shown below each image, with the best values highlighted in red.

In the first set of experiments when the image reconstruction system 100 was used to reconstruct the uniformly-under-sampled T2-weighted datasets, the acquisition of every fourth line of k-space was simulated, while also fully-acquiring the central 24 phase encoding lines to be used as ACS data. This results in an effective acceleration factor of 2.8×.

In the second set of experiments when the image reconstruction system 100 was used to reconstruct the randomly-under-sampled T1-weighted datasets, the acquisition using a variable density Poisson disk random sampling pattern with an effective acceleration factor of 5.2× (including samples from a fully-sampled 64×64 ACS region at the center of k-space) was simulated. In both experiments, the LORAKI network structure (trained with the original ACS data) had significantly lower NRMSE values and significantly higher SSIM values in comparison to the other models. There was very little difference between using synthetic ACS data and original ACS data.

Figure 12C:
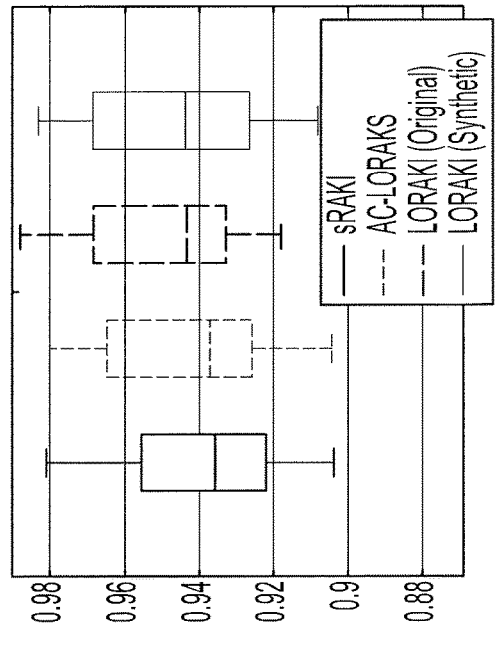
FIG. 12C shows the boxplot performance of NRMSE values measured for T1-weighted data using the different models by the image reconstruction system of FIG. 1 according to an aspect of the invention.
Figure 12D:
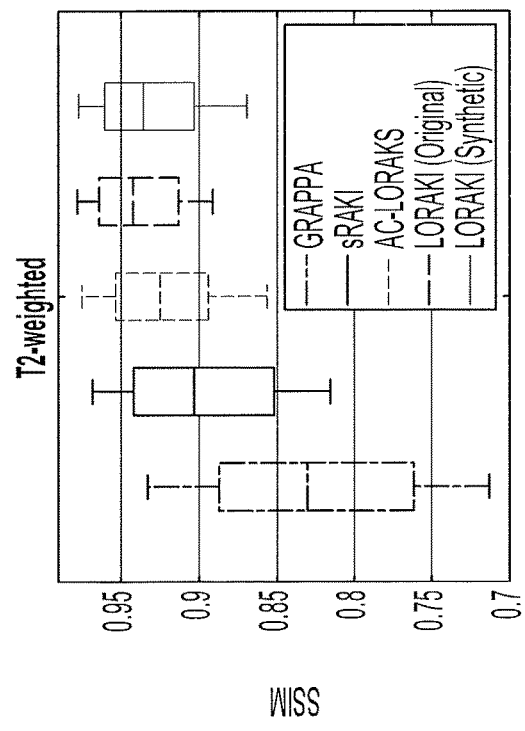
FIG. 12D shows the boxplot performance of the SSIM values measured for T1-weighted data using the different models by the image reconstruction system of FIG. 1 according to an aspect of the invention.
Figure 12A:
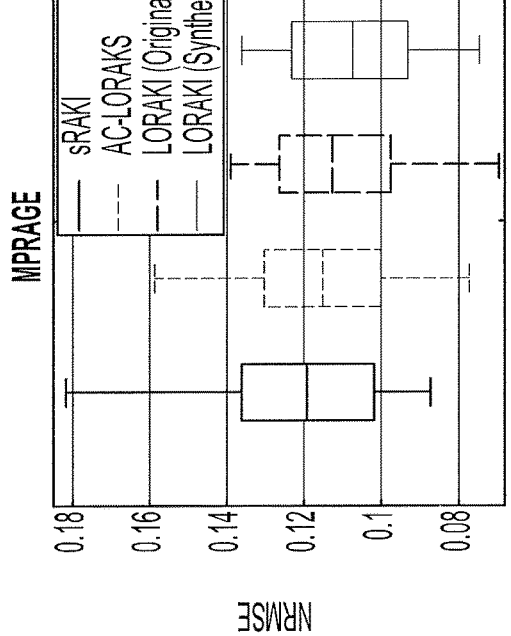
FIG. 12A shows the boxplot performance of NRMSE values measured for T2-weighted data using the different models by the image reconstruction system of FIG. 1 according to an aspect of the invention.
Figure 12B:
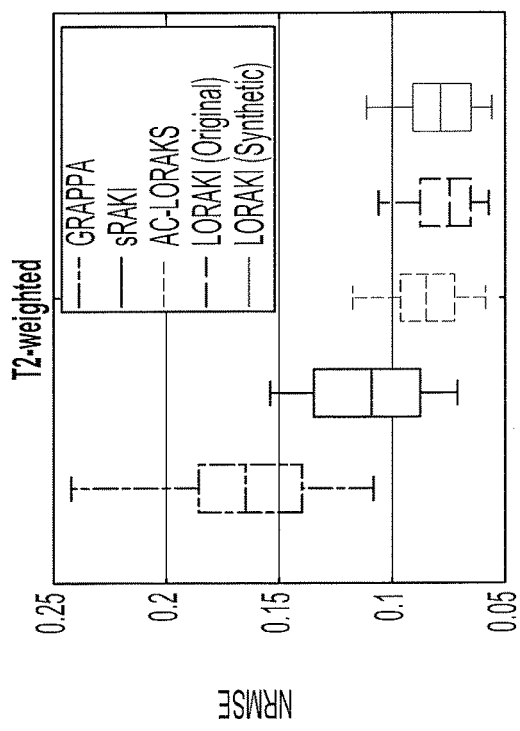
FIG. 12B shows the boxplot performance of the SSIM values measured for T2-weighted data using the different models by the image reconstruction system of FIG. 1 according to an aspect of the invention.

FIG. 11 shows the representative results from one slice of one subject, while numerical results from a total of 50 slices from 5 different subjects are shown in FIGS. 12A-12D. FIGS. 12A and 12C show the boxplot performance of the NRMSE values measured for T2-weighted data and T1-weighted data, respectively, using the different models. FIG. 12B and FIG. 12D show the boxplot performance of the SSIM values measured for T2-weighted data and T1-weighted data, respectively, using the different models. The results are compared using the NRMSE and SSIM. As can be observed, the LORAKI network structure has the best overall performance, with lower RMSE values and higher SSIM values compared to the other reconstruction models.

Figure 13B:
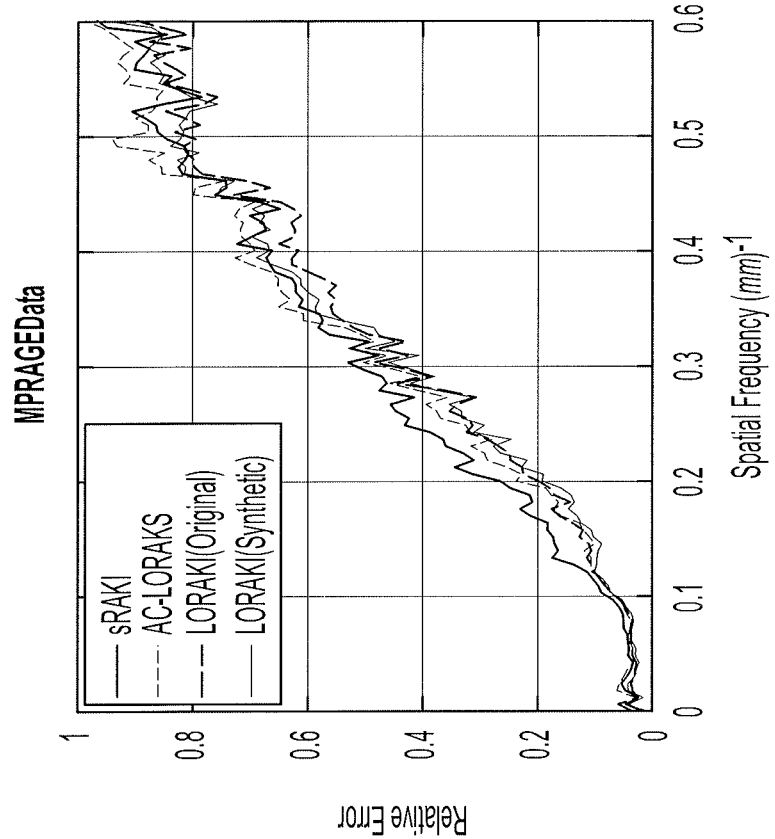
FIG. 13B shows the error spectrum plot that corresponds with the T1-weighted reconstruction results using the image reconstruction system of FIG. 1 according to an aspect of the invention.
Figure 13A:
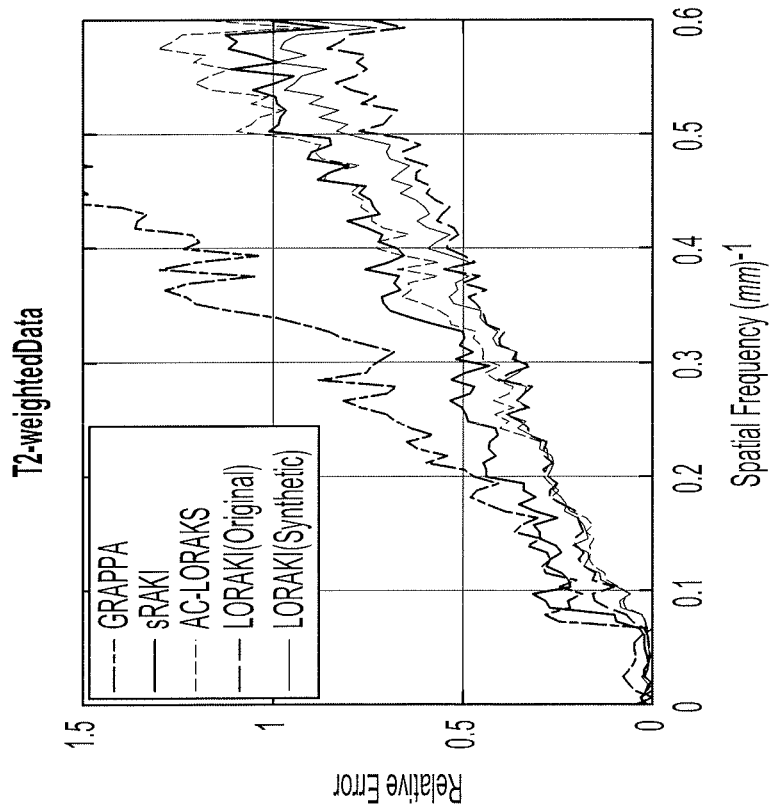
FIG. 13A shows the error spectrum plot that corresponds with the T2-weighted reconstruction results using the image reconstruction system of FIG. 1 according to an aspect of the invention.

FIGS. 13A-13B provide additional information regarding the error characteristics. FIG. 13A shows the error spectrum plot that corresponds with the T2-weighted reconstruction results, and FIG. 13B shows the error spectrum plot that corresponds with the T1-weighted reconstruction results. Thus, the results clearly show that the LORAKI model outperforms the other models in reconstructing a high-quality MRI image. Moreover, the LORAKI model is compatible with a range of different sampling patterns. This demonstrates that the LORAKI model has advantages compared to existing models when sufficient ACS data is available regardless of whether the ACS training data is synthetic or original.

Where used throughout the specification and the claims, "at least one of A or B" includes "A" only, "B" only, or "A and B." Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. An image reconstruction system, comprising:
a memory configured to store a plurality of samples of biological, physiological, neurological or anatomical data with missing or corrupted samples and one or more deep learning models or neural networks, wherein the neural networks includes a recurrent neural network (RNN); and
a processor coupled to the memory and configured to:
obtain the plurality of samples,
determine missing or corrupted k-space samples using the plurality of samples that are under-sampled and the one or more deep learning models or neural networks,
wherein to determine the missing or corrupted k-space samples, the processor is further configured to iterate between performing one or more convolutions and applying a non-linear activation function a number of times to project or generate the missing or corrupted k-space data, wherein the number of times is pre-configured or user-inputted, and
reconstruct a magnetic resonance imaging (MRI) image using the plurality of samples and the determined missing or corrupted k-space.

2. The image reconstruction system of claim 1, wherein the RNN applies the same network layer multiple times and uses at least one non-linear activation function.

3. The image reconstruction system of claim 2, wherein to determine the missing or corrupted k-space samples the processor is configured to:
perform one or more convolutions on the plurality of samples to project the missing or corrupted k-space samples; and
apply the non-linear activation function while performing the one or more convolutions.

4. The image reconstruction system of claim 1, wherein the processor is configured to train parameters of the one or more deep learning models or neural networks using a subset of k-space data that is not missing samples.

5. The image reconstruction system of claim 1, wherein the processor is configured to:
generate the one or more deep learning models or neural networks, wherein the obtained plurality of samples are the only inputs used to generate the deep learning model or neural network.

6. The image reconstruction system of claim 1, wherein the processor is configured to determine the missing or corrupted k-space samples to reconstruct the magnetic resonance image for a plurality of different patterns of under-sampled biological, physiological, neurological or anatomical data.

7. The image reconstruction system of claim 1, further comprising:
a display configured to display the reconstructed MRI image.

8. The image reconstruction system of claim 1, wherein the plurality of samples of biological, physiological, neurological or anatomical data with the missing or corrupted samples are obtained from a single MRI image of only a specific subject.

9. The image reconstruction system of claim 1, wherein the plurality of samples are obtained in a Fourier transform domain and an inverse of the Fourier transform domain is performed to reconstruct the single MRI image, wherein a number of samples of the plurality of samples is less than a Nyquist rate.

10. An image reconstruction system, comprising:
a memory configured to store a plurality of samples of biological, physiological, neurological or anatomical data with missing or corrupted samples and one or more deep learning models or neural networks, wherein the neural networks includes a recurrent neural network (RNN); and
a processor coupled to the memory and configured to:
obtain the plurality of samples;
determine missing or corrupted k-space samples using the plurality of samples that are under-sampled and the one or more deep learning models or neural networks; and
reconstruct a magnetic resonance imaging (MRI) image using the plurality of samples and the determined missing or corrupted k-space,
wherein the RNN applies the same network layer multiple times and uses at least one non-linear activation function,
wherein to determine the missing or corrupted k-space samples the processor is configured to:
perform one or more convolutions on the plurality of samples to project the missing or corrupted k-space samples; and
apply the non-linear activation function while performing the one or more convolutions, and
wherein to determine the missing or corrupted k-space samples the processor is further configured to iterate between the performing the one or more convolutions and applying the non-linear activation function a number of times to project or generate missing or corrupted k-space data, wherein the number of times is pre-configured or user-inputted.

11. An image reconstruction system, comprising:
a memory configured to store a plurality of samples of biological, physiological, neurological or anatomical data with missing or corrupted samples and one or more deep learning models or neural networks, wherein the neural networks includes a recurrent neural network (RNN); and
a processor coupled to the memory and configured to:
train parameters of a first model and a second model using a subset of the k-space data that is complete,
determine a first set of reconstructed k-space data based on a plurality of samples and the first model,
determine a second set of reconstructed k-space data based on the plurality of samples and the second model, obtain the plurality of samples,
determine missing or corrupted k-space samples using the plurality of samples that are under-sampled and the one or more deep learning models or neural networks, and
reconstruct a magnetic resonance imaging (MRI) image using the plurality of samples and the determined missing or corrupted k-space wherein a reconstructed magnetic resonance imaging (MRI) image is further based on the first set and the second set of reconstructed k-space data,
wherein to determine the missing or corrupted k-space samples the processor is further configured to iterate between performing a one or more convolutions and applying a non-linear activation function a number of times to project or generate the missing or corrupted k-space data, wherein the number of times is pre-configured or user-inputted.

12. The image reconstruction system of claim 11, wherein the subset of the k-space data that is complete does not have missing samples, wherein to determine the first set of reconstructed k-space data based on the plurality of samples and the first model the processor is configured to:
determine a first set of missing k-space data based on the first model and the plurality of samples; and
determine the first set of reconstructed k-space data further based on the first set of missing k-space data.

13. The image reconstruction system of claim 11, wherein the processor is further configured to:
determine a first weight for the first set of reconstructed k-space data and a second weight for the second set of reconstructed k-space data; and
reconstruct the magnetic resonance imaging (MRI) image further based on weighted combination of the first and second set of reconstructed k-space data.

14. The image reconstruction system of claim 11, further comprising:
a magnetic resonance imaging (MRI) scanner configured to obtain the plurality of samples of biological, physiological, neurological or anatomical data that include missing or corrupted k-space data.

15. The image reconstruction system of claim 11, wherein the first model is a deep learning model or neural network that uses at least one non-linear activation function, wherein the deep learning model or the neural network is the recurrent neural network (RNN) that applies the same network layer multiple times.

16. The image reconstruction system of claim 15, wherein the non-linear activation function is a rectified linear unit (ReLu) non-linear activation function.

* * * * *